(12) United States Patent
Beers et al.

(10) Patent No.: US 10,297,344 B1
(45) Date of Patent: May 21, 2019

(54) SYSTEMS AND METHODS FOR ESTABLISHING AN INDIVIDUAL'S LONGITUDINAL MEDICATION HISTORY

(71) Applicant: McKesson Corporation, San Francisco, CA (US)

(72) Inventors: Mark Beers, Lilburn, GA (US); Elke Helga Katharina Timmerman, Atlanta, GA (US); James Adair, Alpharetta, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 392 days.

(21) Appl. No.: 14/230,721

(22) Filed: Mar. 31, 2014

(51) Int. Cl.
G06F 19/00 (2018.01)
G16H 10/60 (2018.01)

(52) U.S. Cl.
CPC .................... G16H 10/60 (2018.01)

(58) Field of Classification Search
CPC ...... G06F 19/322; G06F 19/324; G06Q 50/22
USPC .......................................... 705/2, 3
See application file for complete search history.

(56) References Cited

U.S. PATENT DOCUMENTS

| | | | |
|---|---|---|---|
| 4,674,041 A | 6/1987 | Lemon et al. | |
| 4,723,212 A | 2/1988 | Mindrum et al. | |
| 4,910,672 A | 3/1990 | Off et al. | |
| 5,007,641 A | 4/1991 | Seidman | |
| 5,080,364 A | 1/1992 | Seidman | |
| 5,173,851 A | 12/1992 | Off et al. | |
| 5,201,010 A | 4/1993 | Deaton et al. | |

(Continued)

FOREIGN PATENT DOCUMENTS

CA 2482370 A1 3/2006
EP 1310895 A2 11/2002

(Continued)

OTHER PUBLICATIONS

Sampson, R.J., Taking Control of Health Care Costs, Best's Review—Life Health Insurance Edition, Nov. 1983, vol. 84, Issue 7, USA; Abstract only.

(Continued)

*Primary Examiner* — Hiep V Nguyen
*Assistant Examiner* — Trang T Nguyen
(74) *Attorney, Agent, or Firm* — Alston & Bird LLP

(57) ABSTRACT

Systems and methods are provided for generating an individual's longitudinal medication history. Consent to generate an individual's longitudinal medication history across a pharmacy(s) and a claims processor(s) is received. A first collection of medication history data corresponding to the individual is selectively identified from medication history data files associated with the claims processor(s) and a first plurality of individuals. The selective identification is based on a claims processor patient identifier(s) associated with the individual and the claims processor(s). A second collection of medication history data corresponding to the individual is selectively identified from medication history data files associated with the pharmacy(s) and a second plurality of individuals. The selective identification is based on a linking index(s) associated with the claims processor patient identifier(s). An individual's longitudinal medication history is generated, based on the first collection of medication history data and the second collection of medication history data.

20 Claims, 7 Drawing Sheets

(56) References Cited

U.S. PATENT DOCUMENTS

| | | |
|---|---|---|
| 5,235,702 A | 8/1993 | Miller |
| 5,237,620 A | 8/1993 | Deaton et al. |
| 5,301,105 A | 4/1994 | Cummings |
| 5,305,196 A | 4/1994 | Deaton et al. |
| 5,327,508 A | 7/1994 | Deaton et al. |
| 5,359,509 A | 10/1994 | Little et al. |
| 5,388,165 A | 2/1995 | Deaton et al. |
| 5,430,644 A | 7/1995 | Deaton et al. |
| 5,448,471 A | 9/1995 | Deaton et al. |
| 5,465,286 A | 11/1995 | Clare et al. |
| 5,544,044 A | 8/1996 | Leatherman |
| 5,550,734 A | 8/1996 | Tarter et al. |
| 5,588,649 A | 12/1996 | Blumberg et al. |
| 5,592,560 A | 1/1997 | Deaton et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |
| 5,644,723 A | 7/1997 | Deaton et al. |
| 5,644,778 A | 7/1997 | Burks et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,704,044 A | 12/1997 | Tarter et al. |
| 5,748,907 A | 5/1998 | Crane |
| 5,749,907 A | 5/1998 | Mann |
| 5,832,447 A | 11/1998 | Rieker et al. |
| 5,832,457 A | 11/1998 | O'Brien |
| 5,845,255 A * | 12/1998 | Mayaud ............ G06F 19/3456 705/3 |
| 5,857,175 A | 1/1999 | Day et al. |
| 5,892,827 A | 4/1999 | Beach et al. |
| 5,892,900 A | 4/1999 | Ginter et al. |
| 5,915,007 A | 6/1999 | Klapka |
| 5,926,795 A | 7/1999 | Williams |
| 5,950,169 A | 9/1999 | Borghesi et al. |
| 5,956,736 A | 9/1999 | Hanson et al. |
| 5,963,915 A | 10/1999 | Kirsch |
| 5,970,469 A | 10/1999 | Scroggie et al. |
| 5,974,399 A | 10/1999 | Giuliani et al. |
| 5,991,750 A | 11/1999 | Watson |
| 6,006,242 A | 12/1999 | Poole et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,073,104 A | 6/2000 | Field |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,208,973 B1 | 3/2001 | Boyer et al. |
| 6,224,387 B1 | 5/2001 | Jones |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,940 B1 | 10/2001 | Yamamoto et al. |
| 6,307,958 B1 | 10/2001 | Deaton et al. |
| 6,321,210 B1 | 11/2001 | O'Brien et al. |
| 6,324,516 B1 | 11/2001 | Shults et al. |
| 6,330,546 B1 | 12/2001 | Gopinathan et al. |
| 6,334,108 B1 | 12/2001 | Deaton et al. |
| 6,341,265 B1 | 1/2002 | Provost et al. |
| 6,343,271 B1 | 1/2002 | Peterson et al. |
| 6,351,735 B1 | 2/2002 | Deaton et al. |
| 6,377,935 B1 | 4/2002 | Deaton et al. |
| 6,427,020 B1 | 6/2002 | Rhoads |
| 6,424,949 B1 | 7/2002 | Deaton et al. |
| 6,484,146 B2 | 11/2002 | Day et al. |
| 6,584,448 B1 | 6/2003 | Laor |
| 6,632,251 B1 | 10/2003 | Rutten et al. |
| 6,671,692 B1 | 12/2003 | Marpe et al. |
| 6,671,693 B1 | 12/2003 | Marpe et al. |
| 6,684,195 B1 | 1/2004 | Deaton et al. |
| 6,714,918 B2 | 3/2004 | Hillmer et al. |
| 6,769,228 B1 | 8/2004 | Mahar |
| 6,795,809 B2 | 9/2004 | O'Brien et al. |
| 6,879,959 B1 | 4/2005 | Chapman et al. |
| 6,885,994 B1 | 4/2005 | Scroggie et al. |
| 7,013,284 B2 | 3/2006 | Guyan et al. |
| 7,024,374 B1 | 4/2006 | Day et al. |
| 7,046,789 B1 | 5/2006 | Anderson et al. |
| 7,058,584 B2 | 6/2006 | Kosinski et al. |
| 7,058,591 B2 | 6/2006 | Giuliani et al. |
| 7,111,173 B1 | 9/2006 | Scheidt |
| 7,155,397 B2 | 12/2006 | Alexander et al. |
| 7,225,052 B2 | 5/2007 | Foote et al. |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,356,460 B1 | 4/2008 | Kennedy et al. |
| 7,380,707 B1 | 6/2008 | Fredman |
| 7,401,027 B2 | 7/2008 | Moore et al. |
| 7,415,426 B2 | 8/2008 | Williams et al. |
| 7,418,400 B1 | 8/2008 | Lorenz |
| 7,426,480 B2 | 9/2008 | Granger et al. |
| 8,538,777 B1 * | 9/2013 | Kaye ................ G06F 19/3456 705/3 |
| 8,731,966 B2 * | 5/2014 | Breitenstein ................ 705/2 |
| 8,788,287 B2 * | 7/2014 | Padate ............ G06F 19/322 705/3 |
| 2001/0001014 A1 | 5/2001 | Akins, III et al. |
| 2001/0032099 A1 | 10/2001 | Joao |
| 2001/0037216 A1 | 11/2001 | Oscar et al. |
| 2001/0037224 A1 | 11/2001 | Eldridge et al. |
| 2001/0041993 A1 | 11/2001 | Campbell |
| 2002/0002495 A1 | 1/2002 | Ullman |
| 2002/0035484 A1 | 3/2002 | McCormick |
| 2002/0035488 A1 | 3/2002 | Aquila et al. |
| 2002/0044043 A1 | 4/2002 | Chaco et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0073099 A1 * | 6/2002 | Gilbert ............ G06F 17/3061 |
| 2002/0087554 A1 | 7/2002 | Seelinger |
| 2002/0087583 A1 | 7/2002 | Morgan et al. |
| 2002/0111832 A1 | 8/2002 | Judge |
| 2002/0120473 A1 | 8/2002 | Wiggins |
| 2002/0128883 A1 | 9/2002 | Harris |
| 2002/0133503 A1 | 9/2002 | Amar et al. |
| 2002/0138593 A1 | 9/2002 | Novak et al. |
| 2002/0175370 A1 | 11/2002 | Bockelman |
| 2002/0175929 A1 | 11/2002 | Hunt et al. |
| 2002/0183979 A1 | 12/2002 | Wildman |
| 2002/0198831 A1 | 12/2002 | Patricelli et al. |
| 2003/0009357 A1 | 1/2003 | Pish |
| 2003/0009367 A1 | 1/2003 | Morrison |
| 2003/0028404 A1 | 2/2003 | Herron et al. |
| 2003/0050799 A1 | 3/2003 | Jay et al. |
| 2003/0074218 A1 | 4/2003 | Liff et al. |
| 2003/0074222 A1 | 4/2003 | Rosow et al. |
| 2003/0083903 A1 | 5/2003 | Myers |
| 2003/0120588 A1 | 6/2003 | Dodd et al. |
| 2003/0125986 A1 | 7/2003 | Collosi |
| 2003/0149594 A1 | 8/2003 | Beazley et al. |
| 2003/0149625 A1 | 8/2003 | Leonardi et al. |
| 2003/0154163 A1 | 8/2003 | Phillips et al. |
| 2003/0158755 A1 | 8/2003 | Neuman |
| 2003/0229540 A1 | 12/2003 | Algiene |
| 2004/0006490 A1 | 1/2004 | Gingrich et al. |
| 2004/0019464 A1 | 1/2004 | Martucci et al. |
| 2004/0039599 A1 | 2/2004 | Fralic |
| 2004/0046020 A1 | 3/2004 | Andreasson et al. |
| 2004/0054657 A1 | 3/2004 | Takeyama |
| 2004/0073457 A1 | 4/2004 | Kalies |

(56) References Cited

U.S. PATENT DOCUMENTS

| | | |
|---|---|---|
| 2004/0078234 A1 | 4/2004 | Tallal, Jr. |
| 2004/0093242 A1 | 5/2004 | Cadigan et al. |
| 2004/0107117 A1 | 6/2004 | Denny |
| 2004/0111277 A1 | 6/2004 | Pearson et al. |
| 2004/0111291 A1 | 6/2004 | Dust et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0172281 A1 | 9/2004 | Stanners |
| 2004/0188998 A1 | 9/2004 | Henthom |
| 2004/0249745 A1 | 12/2004 | Baaren |
| 2005/0015280 A1 | 1/2005 | Gabel et al. |
| 2005/0033604 A1 | 2/2005 | Hogan |
| 2005/0033610 A1 | 2/2005 | Cunningham |
| 2005/0060201 A1 | 3/2005 | Connely, III et al. |
| 2005/0065821 A1 | 3/2005 | Kalies |
| 2005/0086081 A1 | 4/2005 | Brock-Fisher |
| 2005/0090425 A1 | 4/2005 | Reardan et al. |
| 2005/0102169 A1 | 5/2005 | Wilson |
| 2005/0125292 A1 | 6/2005 | Kassab et al. |
| 2005/0154627 A1 | 7/2005 | Zuzek et al. |
| 2005/0171815 A1 | 8/2005 | Vanderveen |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0246205 A1* | 11/2005 | Wang ............. G06F 19/322 705/3 |
| 2005/0256740 A1* | 11/2005 | Kohan ............. G06F 19/322 705/2 |
| 2005/0288972 A1 | 12/2005 | Marvin et al. |
| 2006/0015518 A1 | 1/2006 | Eletreby et al. |
| 2006/0020514 A1 | 1/2006 | Yered |
| 2006/0026041 A1 | 2/2006 | Ullman |
| 2006/0085230 A1 | 4/2006 | Brill et al. |
| 2006/0149587 A1 | 7/2006 | Hill, Sr. et al. |
| 2006/0149784 A1 | 7/2006 | Tholl et al. |
| 2006/0178915 A1 | 8/2006 | Chao |
| 2006/0184391 A1 | 8/2006 | Barre et al. |
| 2006/0224415 A1 | 10/2006 | Hudson et al. |
| 2006/0229915 A1 | 10/2006 | Kosinski et al. |
| 2006/0247948 A1 | 11/2006 | Ellis et al. |
| 2006/0259363 A1 | 11/2006 | Jhetam et al. |
| 2006/0271398 A1 | 11/2006 | Belcastro |
| 2006/0271405 A1 | 11/2006 | Cipolle et al. |
| 2006/0287886 A1 | 12/2006 | Kitazawa |
| 2007/0005402 A1 | 1/2007 | Kennedy et al. |
| 2007/0050209 A1 | 3/2007 | Yered |
| 2007/0067186 A1 | 3/2007 | Brenner et al. |
| 2007/0088576 A1 | 4/2007 | de Beus et al. |
| 2007/0124177 A1 | 5/2007 | Engleson et al. |
| 2007/0136100 A1 | 6/2007 | Daugherty et al. |
| 2007/0162303 A1 | 7/2007 | Wiley et al. |
| 2007/0179957 A1 | 8/2007 | Gibson et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0147554 A1* | 6/2008 | Stevens ............. G06F 19/322 705/51 |
| 2010/0122202 A1 | 5/2010 | Omiya |
| 2011/0060757 A1* | 3/2011 | Dettinger ............. G06F 19/322 707/769 |
| 2011/0125528 A1* | 5/2011 | Padate ............. G06F 19/322 705/3 |
| 2013/0218599 A1* | 8/2013 | Highley ............. G06Q 30/04 705/3 |
| 2014/0039929 A1* | 2/2014 | Vdovjak ............. G06F 19/322 705/3 |
| 2014/0100880 A1* | 4/2014 | Patterson ............. G06F 19/327 705/3 |
| 2015/0149208 A1* | 5/2015 | Lynch ............. G06F 21/6254 705/3 |
| 2015/0278482 A1 | 10/2015 | Mattera |

FOREIGN PATENT DOCUMENTS

| | | |
|---|---|---|
| WO | 1991006917 A1 | 5/1991 |
| WO | 1995003569 A3 | 2/1995 |
| WO | 1997025682 A1 | 7/1997 |
| WO | 1998050871 A1 | 11/1998 |
| WO | 2000039737 A1 | 7/2000 |
| WO | 2007025295 A2 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, vol. 63, Issue 1, USA; Abstract only.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005.

Hutty, S. Third party issues: Understanding drug benefits for better patient care. Pharmacy Practice, 18(6), CE1-CE16, Retrieved from http://search.proquest.com/docview/232078749?accountid=14753.

Nonfinal Office Action for U.S. Appl. No. 12/165,031 dated Nov. 23, 2010.

Final Office Action for U.S. Appl. No. 12/165,031, dated Apr. 13, 2011.

Non-Final Office Action for U.S. Appl. No. 13/181,082 dated Feb. 20, 2013.

Notice of Allowance for U.S. Appl. No. 12/165,031 dated May 15, 2013.

Final Office Action for U.S. Appl. No. 13/181,082 dated Jul. 24, 2013.

Non-Final Office Action for U.S. Appl. No. 14/010,167 dated Jun. 9, 2014.

Letter Restarting Period for Response for U.S. Appl. No. 14/010,167 dated Jul. 10, 2014.

Final Office Action for U.S. Appl. No. 14/010,167 dated Feb. 26, 2015.

Non-final Office Action for U.S. Appl. No. 14/010,167 dated Sep. 4, 2015.

* cited by examiner

SYSTEMS AND METHODS FOR ESTABLISHING AN INDIVIDUAL'S LONGITUDINAL MEDICATION HISTORY

TECHNICAL FIELD

Aspects of the disclosure relate generally to patient medication histories, and more particularly, to systems and methods for aggregating a patient's medication history across multiple covered entities to establish the patient's longitudinal medication history across the multiple covered entities.

BACKGROUND

An individual's longitudinal medication history can include a chronological history of medications the patient has taken over a period of time. One measure of a patient's longitudinal medication history can include the number and types of over the counter ("OTC") medications and/or prescription medications a patient has purchased over a time period. In general, an individual goes to a pharmacy to purchase OTC medications and/or prescription medications. However, an individual's identification information, the pharmacy they purchase medications from, and/or the health insurance company they have can change over a period of time. Correspondingly, an individual's medication history can be distributed over many covered entities (e.g., insurance companies and pharmacies) during a given time period. For example, an individual may go to different pharmacies to have their prescriptions filled and/or to purchase OTC medications. In such an example, an individual's medication history is distributed over multiple pharmacies. In another example, the individual may get their medications from store A of Pharmacy Chain in City A and Store B of Pharmacy Chain in City B. In such an example, the pharmacy chain may identify the patient as two distinct individuals because the individual's identification information (e.g., the patient's address) has changed. Accordingly, it can be difficult to accurately establish a patient's longitudinal medication history because, for example, a patient's medication information can be distributed over multiple covered entities and/or distributed with different identification information.

Furthermore, patient privacy regulations can complicate establishing an individual's longitudinal medication history. Patient privacy regulations can include, but are not limited to, rules promulgated by the Department of Health & Human Services ("HHS") pursuant to the Health Insurance Portability and Accountability Act ("HIPPA") and the Health Information Technology for Economic and Clinical Health ("HITECH") Act. Such patient privacy regulations limit what type of and how patient information can be shared among covered entities absent patient consent or contractual relationship between covered entities. For example, patient privacy regulations do not allow patient medication history data to be shared across the same type of covered entity absent an individual's consent (e.g., distinct pharmacy are not permitted to share patient medication history data absent an individual's consent). Furthermore, even when consent is given by an individual, patient privacy regulations do not permit another individual's information data to be accessed even if only to determine the other individual is not the individual who gave consent. Accordingly, it can be difficult to establish the full scope of a patient's medication history over long periods of time in accordance with applicable patient privacy regulations.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Figure 1:
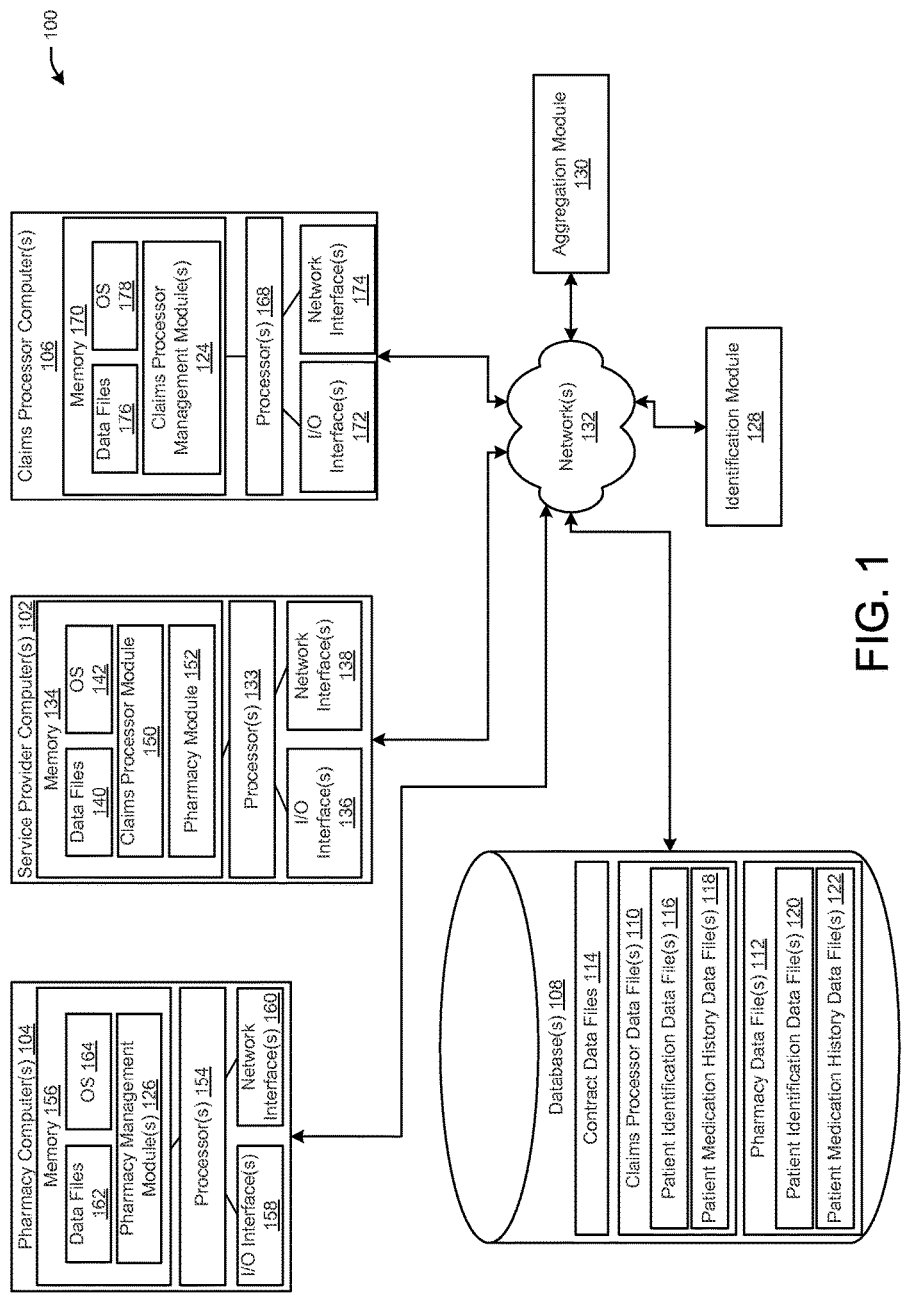
FIG. 1 illustrates an example system for establishing an individual's longitudinal medication history, in accordance with one example embodiment of the disclosure.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods that facilitate the establishment of an individual's longitudinal medication history, in accordance with privacy regulations. In some example embodiments, the systems and methods generate linking indexes to link an individual's medication history data across one or more pharmacies and one or more claims processors (e.g., a Pharmacy Benefits Manager (PBM), claims payor, healthcare insurance company, Medicare, Medicaid, or other government healthcare insurance payor, Medicare Part D provider, claims clearinghouse, etc.). As used herein, a pharmacy refers to all pharmacy stores doing business under a given name, unless explicitly referred to otherwise. For example, a pharmacy refers to the all stores of a pharmacy chain (e.g., CVS and Walgreens pharmacy). The linking indexes can be generated from patient identification data gathered by the system in accordance with patient privacy regulations. In some example embodiments, the systems and methods can generate a linking index for one or more individuals relative to one or more pharmacies and/or one or more claims processor computers associated with one or more claims processors. For example, a linking index can be generated for an individual relative to a single pharmacy, multiple pharmacies, a single claims processor, multiple claims processors, or any combination thereof. In such an example, the linking index can correspond to a unique individual identified from the patients represented by patient identification data from a single pharmacy, multiple pharmacies, a single claims processor, multiple claims processors, or any combination thereof. In certain example embodiments, the systems and methods described herein can desirably generate linking indexes for an individual over single pharmacies and over multiple claims processors. In some example embodiments, an individual can consent to having the individual's longitudinal medication history established over a selected group of pharmacies, claims processors, or pharmacies and claims processors. In such embodiments, the systems and methods described herein can link the individual's medication history over the selected group of pharmacies, claims processors, or pharmacies and claims processors using the linking indexes for the individual.

Patient privacy regulations (e.g., HIPAA and/or HITECH) can restrict what type of, and how, patient information data (e.g., patient identification data and patient medication history data) can be shared between covered entities. Covered entities include, but are not limited to, claims processors (e.g., a Pharmacy Benefits Manager (PBM), claims payor, healthcare insurance company, Medicare, Medicaid, or other government healthcare insurance payor, Medicare Part D provider, claims clearinghouse, etc.) and pharmacies. For example, patient privacy regulations, in general, do not allow different covered entities to share patient medication history data, absent patient consent. As another example, even where an individual's consent exists, privacy regulations only allow those records belonging to that individual to be accessed to establish a longitudinal patient medication history for that individual (i.e., medication history records belonging to another individual may not be accessed, even if only to determine that those records belong do not belong to the same individual who's longitudinal medication history is being established). On the other hand, patient privacy regulations do allow distinct claims processors to share patient identification information data (described in detail below). However, even in such situations, patient identification information data can only be shared between distinct claims processors that are parties to a data rights management agreement(s).

In some example embodiments, a service provider computer can generate an individual's longitudinal medication history based at least in part upon patient information data that is collected by the service provider computer, in accordance with patient privacy regulations and incident to the service provider computer providing services for covered entities. For example, a service provider computer can, according to patient privacy regulations, collect patient identification data including, but not limited to, patient demographic data and/or billing data from a given claims processor computer in response to the claims processor computer's (i.e., a computer located within or providing computing services for a claims processor) request to sign-up one or more individuals for Eligibility Services, including, but not limited to, immunization opportunity identification, cash medication regimen tracking, and/or medication therapy management ("MTM"). In some example embodiments and in accordance with patient privacy regulations, a claims processor computer can sign-up one or more individuals who receive health insurance coverage from the claims processor associated with the claims processor computer. As another example, a service provider computer can collect patient identification data for a given pharmacy computer in response to the pharmacy associated with (i.e., located within or providing primary computing services for) the pharmacy computer's request to sign-up for services related to billing transaction processing and/or Eligibility Services between the pharmacy computer and the claims processor computer.

In certain example embodiments, based at least in part on the collected patient identification data, a service provider computer can generate linking indexes to link an individual patient's medication history data across a pharmacy and/or one or more claims processors. In some example embodiments, the service provider computer can identify individuals associated with one or more covered entities from patient identification information collected by the service provider computer incident to performing services for those one or more covered entities. For example, the service provider computer can identify individuals from a set of patient identification data received from one or more pharmacy computers and/or one or more claims processor computers. For example, the service provider computer can generate a linking index for each identified individual and associate the linking index with a unique identifier ("individual longitudinal identifier," discussed below). The linking index can include one or more keys corresponding to distinct patients, representing the same individual, in the set of patient identification data. For example, the set of patient identification data can correspond to patient identification data received from a pharmacy computer associated with a pharmacy. In such embodiments, an individual may be represented by two (or more) distinct patient identification data (i.e., the pharmacy can have two (or more) distinct patient records for the same individual) and the service provider computer can create a key for each of the two (or more) distinct representations of the individual in the patient identification records received from the pharmacy computer. As used herein, "patient" refers to a covered entity's representation of an "individual" through patient identification data.

In some example embodiments, a key can include one or more key fields and corresponding key values. The example key fields can be selected from some or all of the patient identification data collected by the service provider computer. Example keys associated with different covered entities can have one or more common key fields. When the service provider computer receives a notification of an individual's consent to establish the individual's longitudinal medication history across covered entities, or any subset thereof, the service provider computer can link the individual's medication histories across different covered entities by searching for common keys among the linking indexes associated with each covered entity. In such an example embodiment, the service provider computer can selectively identify an individual's medication history across one or more pharmacies and one or more claims processors (i.e., the service provider computer does not access any other individual's patient information data) and generate an individual's longitudinal medication history.

System Overview

FIG. 1 illustrates an example system 100 for facilitating, among other things, establishing a longitudinal patient medication history according to one example embodiment of the disclosure. As shown in FIG. 1, the system 100 may include one or more service provider computers 102, one or more pharmacy computers 104, and/or one or more claims processor computers 106. The one or more pharmacy computers 104 and/or one or more claims processor computers 106 can be respectively associated with one or more pharmacies (including, but not limited to, hospitals, clinics, or other entities dispensing medications) and/or one or more claims processors. As desired, each of the service provider computers 102, pharmacy computers 104, and/or claims processor computers 106 may include one or more processing devices that may be configured for accessing and reading associated computer-readable media having stored data thereon and/or computer-executable instructions for implementing various embodiments of the disclosure.

The example service provider computer 102 may include, but is not limited to, any suitable processor-driven device that is configured for receiving, processing, and fulfilling medication services between healthcare providers (including, but not limited to, hospitals, clinics, physician's offices, and prescribers of medication), the pharmacy computers 104, and/or claims processor computers 106. Medication services can include, but are not limited to, data related to patient demographic information data (e.g., patient date of birth, patient gender, patient zip/postal code, patient marital status, and number of family members), patient billing information (e.g., patient first name, patient last name, spouse first name, spouse last name, patient street address, cardholder ID, national provider identifier ("NPI")), and/or data related to patient medication history (e.g., medication identifier (i.e., medication name, National Drug Code (NDC) code, Rx number, etc.) and dosage). Any number of pharmacy computers 104, and/or claims processor computers 106 may be in communication with the service provider computer 102 as desired in various example embodiments via, for example, the network 132.

Generally, network devices and systems, including one or more service provider computers 102, pharmacy computers 104, and/or the claims processor computers 106, may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine. As used herein, the term "computer-readable medium" describes any medium for storing computer-executable instructions.

As shown in FIG. 1, the one or more service provider computers 102, pharmacy computers 104, and/or the claims processor computers 106 may be in communication with each other via one or more networks, such as network 132, which may include one or more independent and/or shared private and/or public networks including the Internet or a publicly switched telephone network. In other example embodiments, one or more components of the system 100 may communicate via direct connections and/or communication links. Each of these components—the service provider computer 102, the pharmacy computer 104, the claims processor computer 106, and the network 132—will now be discussed in further detail. Although the components are generally discussed as singular components, as may be implemented in various example embodiments, in alternative exemplary embodiments each component may include any number of suitable computers and/or other components.

With continued reference to FIG. 1, one or more service provider computers 102 may be associated with (i.e., located within) a service provider, such as a healthcare transactions switch. The exemplary service provider computer 102 may include, but is not limited to, any suitable processor-driven device that is configured for receiving, processing, and fulfilling patient medication services from the pharmacy computers 104 and/or the claims processor computer 106. Patient medication services include, but are not limited to eligibility services and medication billing services (e.g., healthcare transactions (such as predetermination of benefits transactions, X-12 270/271 eligibility verification requests, healthcare claim transactions, prescription claim or billing requests, healthcare order transactions, or e-prescription transactions (i.e., electronic prescription order transactions, e-scripts, or e-prescriptions))), requested by the pharmacy computers 104 (on behalf of pharmacies) and the claims processor computers 106 (on behalf of the claims processors). Any number of pharmacy computers 104, and/or claims processor computers 106 may be in communication with the service provider computer 102 as desired in various example embodiments.

The service provider computer 102 may include one or more processors 133, one or more memory devices 134, one or more input/output ("I/O") interfaces 136, and one or more network interfaces 138. The one or more memory devices 134 may be any suitable memory device, for example, caches, read only memory devices, random access memory devices, magnetic storage devices, removable memory devices, etc. The one or more memory devices 134 may store data, executable instructions, and/or various program modules utilized by the service provider computer 102, for example, data files 140 and an operating system ("OS") 142. The OS 142 may be any operating system known in the art or which may be developed in the future including, but not limited to, Microsoft Windows®, Apple OSX™, Linux, Unix, Apple iOS™, Google Android™, or a mainframe operating system. The OS 142 may be a suitable software module that controls the general operation of the service provider computer 102 and/or that facilitates the execution of other software modules.

The service provider computer 102 may include any number of special-purpose computers or other particular machines, application-specific integrated circuits, microcontrollers, personal computers, minicomputers, mainframe computers, servers, networked computers, and/or other processor-driven devices. In certain embodiments, the operations of the service provider computer 102 may be controlled by computer-executed or computer-implemented instructions that are executed by one or more processors associated with the service provider computer 102 to form a special-purpose computer or other particular machine that is operable to facilitate the receipt, routing, and/or processing of healthcare requests or healthcare transactions. The one or more processors that control the operations of the service provider computer 102 may be incorporated into the service provider computer 102 and/or may be in communication with the service provider computer 102 via one or more suitable networks. In certain example embodiments, the operations and/or control of the service provider computer 102 may be distributed among several processing components.

According to an example embodiment, the data files 140 may store patient identification data and patient medication history data associated with communications received from various pharmacy computers 104 and/or various claims processor computers 106. The data files 140 may also store any number of suitable routing tables that facilitate determining the destination of communications received from the claims processor computer 106 and/or the pharmacy computer 104. In one or more example embodiments of the disclosure, the service provider computer 102 may include or otherwise be in communication with one or more suitable databases and/or data storage devices 108 including, but not limited to, one or more patient identification data files 116, 120 and patient medication history data files 118, 122.

The service provider computer 102 may include additional program modules for performing other processing methods described herein. Those of ordinary skill in the art will appreciate that the service provider computer 102 may include alternate and/or additional components, hardware, or software without departing from the scope of the disclosure. For example, the service provider computer 102 may include the claims processor module 150 and/or the pharmacy module 152. The claims processor module 150 can include computer-executable instructions for facilitating, among other things, receipt and/or communication of patient identification data and, optionally, patient medication history data from the claims processor computer 106 (e.g., the claims processor management module 124 or another module associated with a back-end system including one or more of the computers of claims processor computer 106). In some example embodiments, patient identification data and, optionally, patient medication history data can be provided to claims processor module 150 from one or more computers associated with any entity transacting through service provider computer 102 including, but not limited to, a Pharmacy Benefits Manager ("PBM"), claims payor, healthcare insurance company, Medicare, Medicaid, or other government healthcare insurance payor, Medicare Part D provider, claims clearinghouse, etc. The pharmacy module 152 can include computer-executable instructions for facilitating, among other things, receipt and/or communication of patient identification data and patient medication history data from the pharmacy computer 104 (e.g., the pharmacy management module 126). In certain exemplary embodiments, the claims processor module 150 may be implemented as computer-implemented instructions of the memory 134 of the service provider computer 102 or otherwise may be located within the service provider computer 102. Alternatively, the claims processor module 150 may also be implemented as computer-implemented instructions of a memory of a separate computing entity or processor-based system, according to another example embodiment of the disclosure.

In one example implementation, the claims processor module 150 can be operative to receive identifiers, patient identification data and, optionally, patient medication history data, from the claims processor management module 124 of the claims processor computer 106. In one example embodiment, the claims processor module 150 can communicate the received identifiers and patient identification data to the database 108 and store the data in patient identification data files 116 or otherwise store the data in the data files 140. If the claims processor module 150 receives patient medication history data from the claims processor management module 124, the claims processor module 150 can communicate the received patient medication history data to database 108 and/or the data files 140 and store the received data in the patient medication history data files 118.

As another example, the pharmacy module 152 can be operative to receive patient identification data and patient medication history data from the pharmacy management module 126. The pharmacy module 150 can communicate the received patient identification data and patient medication history data to the database 108 and store the data in patient identification data files 120 and patient medication history data 122, respectively. Alternatively, the pharmacy module 150 can store the data in the data files 140.

With continued reference to the service provider computer 102, the one or more I/O interfaces 136 may facilitate communication between the service provider computer 102 and one or more input/output devices, for example, one or more user interface devices, such as a display, keypad, control panel, touch screen display, remote control, microphone, etc., that facilitate user interaction with the service provider computer 102. The one or more network interfaces 138 may facilitate connection of the service provider computer 102 to one or more suitable networks, for example, the network 132 illustrated in FIG. 1. In this regard, the service provider computer 102 may communicate with other components of the system 100. The network interfaces 138 each may take any of a number of forms, such as a network interface card, a modem, a wireless network card, and the like.

With continued reference to FIG. 1, any number of pharmacy computers 104 may be associated with any number of pharmacies and/or pharmacists. Each pharmacy computer 104 may be any suitable processor-driven device that facilitates transmission of healthcare transactions including, but not limited to, predetermination of benefits transactions, X-12 270/271 eligibility verification requests, healthcare claim transactions, prescription claim or billing requests, healthcare order transactions, or e-prescription transactions (i.e., electronic prescription order transactions, e-scripts, or e-prescriptions), to the service provider computer 102. For example, a pharmacy computer 104 can be a processor-driven device associated with (i.e., located within and/or providing primary computing services for) a pharmacy. As desired, the pharmacy computer 104 may include any number of special-purpose computers or other particular machines, application-specific integrated circuits, microcontrollers, personal computers, minicomputers, mainframe computers, servers, tablet computers, smart phones, personal data assistants, and the like. In certain example embodiments, the operations of the pharmacy computer 104 may be controlled by computer-executed or computer-implemented instructions that are executed by one or more processors associated with the pharmacy computer 104 to form a special-purpose computer or other particular machine that is operable to transmit patient healthcare transactions to the service provider computer 102 (e.g., predetermination of benefits transactions, X-12 270/271 eligibility verification requests, healthcare claim transactions, prescription claim or billing requests, healthcare order transactions, or e-prescription transactions (i.e., electronic prescription order transactions, e-scripts, or e-prescriptions)). The one or more processors that control the operations of a pharmacy computer 104 may be incorporated into the pharmacy computer 104 and/or may be in communication with the pharmacy computer 104 via one or more suitable networks. In certain example embodiments, the operations and/or control of the pharmacy computer 104 may be distributed among several processing components.

Similar to other components of the system 100, each pharmacy computer 104 may include one or more processors 154, one or more memory devices 156, one or more I/O interfaces 158, and one or more network interfaces 160. The one or more memory devices 156 may be any suitable memory devices, for example, caches, read-only memory device, random access memory devices, magnetic storage devices, removable memory devices, etc. The one or more memory devices 156 may store data, executable instructions, and/or various program modules utilized by the pharmacy computer 104, for example, data files 162, an OS 164, and a pharmacy management module 126. The data files 162 may include any suitable information that is utilized by the pharmacy computer 104. The OS 164 may be a suitable software module that controls the general operation of the pharmacy computer 104. The OS 164 may also facilitate the execution of other software modules by the one or more processors 154. The OS 164 may be any operating system known in the art or which may be developed in the future including, but not limited to, Microsoft Windows®, Apple OSX™, Linux, Unix, Apple iOS™, Google Android™, or a mainframe operating system.

The one or more I/O interfaces 158 may facilitate communication between the pharmacy computer 104 and one or more input/output devices, for example, one or more user interface devices, such as a display, keypad, control panel, touch screen display, remote control, microphone, etc., that facilitate user interaction with the pharmacy computer 104. The one or more network interfaces 160 may facilitate connection of the pharmacy computer 104 to one or more suitable networks, for example, the network 132 illustrated in FIG. 1. In this regard, the pharmacy computer 104 may transmit healthcare transactions, patient medication history data, and/or other communications to the service provider computer 102. The network interfaces 160 each may take any of a number of forms, such as a network interface card, a modem, a wireless network card, and the like.

The pharmacy management module 126 may be a software application(s), including a dedicated program, for transmitting healthcare transactions, reading and/or updating medical records (e.g., prescription records), facilitating patient billing, etc., as well as interacting with the service provider computer 102. For example, a pharmacist or other pharmacy employee, may utilize the pharmacy management module 126 in filling a prescription, recording and/or updating a patient's medical prescription history, billing a patient and/or claims processor, and preparing and providing a healthcare transaction request for information to the service provider computer 102. Furthermore, the pharmacy computer 104 may utilize the pharmacy management module 126 to retrieve or otherwise receive data, messages, or responses from other components of the system 100.

The claims processor computer 106 may be one or more processor-driven devices, such as, but not limited to, a server computer, a personal computer, a laptop computer, a handheld computer, a tablet computer, a smart phone, and the like. In addition to having one or more processors 168, the claims processor computer 106 may further include one or more memory devices 170, one or more input/output (I/O) interfaces 172, and one or more network interfaces 174. The one or more memory devices 170 may store data files 176 and various program modules, such as an operating system (OS) 178 and a claims processor management module 124. In one example embodiment, the data files 176 can include patient identification data files and associated patient medication history data files. In some such embodiments, the data files 176 can include an identifier that associates the patient identification files and patient medication history data files with a particular individual. The I/O interface 172 may facilitate communication between the processors 168 and various I/O devices, such as a keyboard, mouse, printer, microphone, speaker, monitor, bar code reader/scanner, RFID reader, and the like. The one or more network interfaces 174 may facilitate connection of the claims processor computer 106 to one or more suitable networks, for example, the network 132 illustrated in FIG. 1. In this regard, the claims processor computer 106 may transmit adjudication determinations for healthcare transactions, patient medication history data, and/or other communications to the service provider computer 102. The network interfaces 174 each may take any of a number of forms, such as a network interface card, a modem, a wireless network card, and the like.

Generally, the claims processor computer 106 may facilitate the determination of benefits, coverage, and/or extent of coverage for one or more healthcare transactions, such as prescription claim transactions or other healthcare service or product claim transactions. According to various example embodiments, the claims processor computer 106 may be associated with, without limitation, a PBM, an insurance company, a government payor affiliated entity, another third-party payor, or a claims processor processing healthcare claim transactions and performing adjudication on behalf of one or more third-party payors and/or healthcare providers. In one example embodiment, the claims processor computer 106 may be operated by, or otherwise included with, the service provider computer 102, such as if the service provider operates the claims processor computer 106 and provides adjudication services.

The claims processor computer 106 may include the claims processor management module 124. The claims processor management module 124 may be an Internet browser or other software, such as a dedicated program, for interacting with the service provider computer 102 and/or the pharmacy computer 104.

In one or more example embodiments of the disclosure, the service provider computer 102 may include or otherwise be in communication with one or more suitable databases and/or data storage devices 108. The one or more databases 108 may include one or more data files comprising data including, but not limited to, claims processor data files 110, the pharmacy data files 112, and contract data files 114. Claims processor data files 110 can include, but are not limited to, patient identification data files 116 and patient medication history data files 118. The pharmacy data files 112 can include, but are not limited to, patient identification data files 120 and patient medication history data files 122. In some example embodiments, the database 108 can include separate claims processor data files 110 corresponding to each distinct claims processor associated with claims processor computer 106 and/or separate pharmacy data files 112 corresponding to each distinct pharmacy associated with the pharmacy computer 104. In such embodiments, the database 108 can keep patient information data files and patient medication history data files corresponding to different claims processors and/or different pharmacies separate form one-another (i.e., not commingled).

The one or more patient identification data files 116 and patient medication history data files 118 can contain patient identification information and patient medication history information, respectively, received from the claims processor computer 106. In one example implementation, the claims processor management module 124 can communicate the patient identification data and/or patient medication history data to the service provider computer 102. The service provider computer 102 can facilitate storage of the patient identification data in the patient identification data file 116 and patient medication history data in patient medication history data file 118. The identification data files 120 and patient medication history data files 122 can contain patient identification information and patient medication history information, respectively, received from the pharmacy computer 104. In some example embodiments, a plan sponsor or sponsors (e.g, payer, etc.) when contracting through a PBM may transmit the one or more patient identification data files 116 and patient medication history data files 118 directly to the service provider computer 102 through the network 132. In one example implementation, the pharmacy management module 126 can communicate the patient identification information data and/or patient medication history data to the service provider computer 102. The service provider computer 102 can facilitate storage of the patient identification data in patient identification data file 120 and patient medication history data in patient medication history data file 122.

Patient identification data communicated to the service provider computer 102 from the pharmacy computer 104 and/or the claims processor computer 106 can include, but is not limited to, name (e.g., patient last name, patient first name, etc.), date of birth of patient, age of patient, patient gender (e.g., gender code), patient address (e.g., street address, city, state/province, zip/postal code, etc.), patient contact information (e.g., patient telephone number, email address, etc.), patient identification identifier (such as, but not limited to, patient social security number, a subset of the patient social security number, health insurance claim number (HICN), cardholder ID, etc.), cardholder name (e.g., cardholder first name, cardholder last name), cardholder ID and/or other identifier (e.g., person code), group ID and/or group information, prescriber primary care provider ID or other identifier (e.g., National Provider Identifier (NPI) code), primary care provider name (e.g., last name, first name), prescriber ID or other identifier (e.g., NPI code, Drug Enforcement Administration (DEA) number), prescriber name (e.g., last name, first name), prescriber contact information (e.g., telephone number, email address, fax number), pharmacy or other healthcare provider information (e.g., store name, chain ID), and/or pharmacy or other healthcare provider ID (e.g., NPI code). Patient medication history data communicated to the service provider computer 102 from the pharmacy computer 104 and/or the claims processor computer 106 can include, but is not limited to, drug, service, or product information (e.g., via NDC code or drug/service/product name), prescription/service reference number, date prescription was written, quantity dispensed, days' supply, diagnosis/condition, pricing information for the drug/service/product (e.g., network price, usual & customary price), number of refills authorized, one or more drug utilization (DUR) codes, and date of service.

The one or more contract data files 114 can include contract information between the service provider associated with the service provider computer 102 and the pharmacy associated with the pharmacy computer 104, and between the service provider associated with the service provider computer 102 and the claims processor associated with the claims processor computer 106. The contract information can include information relating to what services the service provider computer 102 is authorized to perform on behalf of the pharmacy computer 104 and/or the claims processor computer 106. Contract information related to the claims processor computer 106 can include, but is not limited to, an indication of whether the service provider computer 102 is authorized to perform an eligibility service on behalf of the claims processor computer 106. Contract information related to the pharmacy computer 104 includes, but is not limited to, whether the service provider computer 102 is authorized to perform billing services on behalf of the pharmacy computer 104. In some example embodiments, contract data files 115 can comprise contract information relating to data rights management that authorize service provider computer 102 to share patient identification data between distinct claims processors. In some such example embodiments, the contract information relating to data rights management can comprise a listing of each claims processor and, for each claims processor, a listing of with which other claims processors service provider computer 102 is authorized to share the claims processor's patient identification data. In some example embodiments, the service provider can require that, as a term of service, all claims processors signing-up for eligibility services authorize service provider computer 102 to share patient identification data between all claims processor computers 106 that are signed-up for eligibility services).

In one or more example embodiments of the disclosure, the service provider computers 102 can also include or otherwise be in communication with the identification module 128 or an individual identification application. The identification module 128 may include computer-executable instructions operable for identifying distinct individuals from patient identification data files, such as patient identification files 116, 120. Over a given time period, an individual's information may change. Changes in an individual's information can include, but are not limited to, changes in health insurance plan, health insurance providers, and health insurance health plan information (e.g., claims processor), residential addresses, and/or name. Correspondingly, an individual's identification data can be different for different covered entities. For example, Store A of Pharmacy in City A may have patient identification data for a customer named "Jane Doe". Store B of Pharmacy in City B may have patient identification data for a customer named "Jane Doe." It is not clear, on its face, whether the patient identification data at Store A and Store B belong to the same individual (e.g., "Jane Doe" may have moved from City A to City B or simply decided to use a different pharmacy store for filling separate prescriptions) or if the patient identification data refers to two distinct individuals (e.g., two different people with the same name, "Jane Doe"). Accordingly, in some example embodiments, the identification module 128 can include computer-executable instructions to apply probabilistic matching techniques to patient identification data to determine if the patient identification data is for the same person.

In certain example embodiments, the computer-executable instructions of the identification module 128 are operable to restrict individual identification logic in accordance with patient privacy regulations. For example, as discussed above, patient privacy regulations, in general, do not allow different covered entities to share patient data. As such, in one example embodiment, the identification module 128 can restrict patient identification logic to the patient identification data files 116, 120 of each claims processor associated with each claims processor computer 106 and/or of each pharmacy (or store thereof, or any combination of stores thereof) associated with one or more pharmacy computers 104. In such embodiments, the identification module 128 can identify individuals associated with each claims processor/claims processor computer 106 and/or each pharmacy/pharmacy computer 104. Privacy regulations, however, do allow different claims processors to share patient identification information. Thus, in some example embodiments, the identification module 128 can apply individual identification logic across patient identification data files 116 associated with one or more claims processors/claims processor computers 106. In such embodiments, the identification module 128 can identify individuals across all the claims processor entities or any subset(s) thereof.

The identification module 128 can include computer-executable code for generating a linking index from the patient identification data files 116 and 120. A linking index can include one or more keys that can be used to identify an individual's patient medication history data within different covered entities or any combination thereof, based at least in part on how the identification module 128 applies individual identification logic. In some example embodiments, the identification module 128 can generate a linking index for each individual relative to one or more covered entities. For example, identification module 128 can apply individual identification logic to generate an individual's linking index over one or more stores of a pharmacy/pharmacy computer 106, over one or more pharmacies/pharmacy computer 106, and/or over one or more claims processors/claims processor computer 106. As another example, the identification module 128 can apply individual identification logic to generate a linking index for a single pharmacy/pharmacy computer 104 and can independently apply individual identification logic to generate a linking index for multiple claims processor entities/claims processor computer 106. In such an embodiment, the identification module 128 can generate a linking index for each individual identified from the patient identification data files 116 corresponding to the single pharmacy/pharmacy computer 104 and can generate a linking index for each individual identified from the patient identification data files 116 corresponding to the multiple claims processor/claims processor computers 106. In some example embodiments, as explained in detail below, the keys can link an individual's linking indexes across different covered entities. Returning to the previous example, the one or more keys in an individual's linking index corresponding to the single pharmacy/pharmacy computer 104 can be used to identify that individual's linking index corresponding to the multiple claims processor/claims processor computer 106.

In some example embodiments, identification module 128 can also generate an individual longitudinal identifier for each linking index or group of linking indexes. The individual longitudinal identifier can include an alphabetical, numeric, or alphanumeric string of characters (e.g., "abcdef," "1a2b3c" or "12345," respectively). The individual longitudinal identifier can be directly or indirectly linked to an individual's patient medication history corresponding to the one or more covered entities over which the linking index or linking indexes are established. For example, a linking index can be generated over one or more stores of a pharmacy, one or more pharmacies and/or one or more claims processors from patient identification data files provided by, respectively, the one or more stores of a pharmacy/pharmacy computer 104, the one or more pharmacy/pharmacy computer 104 and/or the one or more claims processor/claims processor computer 106. In another example, a linking index can be generated from the patient identification data files 120 corresponding to a single pharmacy. In such an example, the identification module 128 can generate a individual longitudinal identifier for the individual and link the identifier to the patient medication history of the individual in the patient medication history data files 122 corresponding to the single pharmacy. In a further example, a linking index can be generated from the patient identification files 116 corresponding to multiple claims processors. In such an example, the identification module 128 can generate a individual longitudinal identifier for the individual and link the identifier to the patient medication history of the individual in patient medication history data files 118 corresponding to the multiple claims processors.

The identification module 128 can access the database 108 and store the one or more linking indexes therein. For example, the identification module 128 can store linking indexes generated from the patient identification data files 116 with the claims processor data files 110 and indexes generated from the patient identification data files 120 with the pharmacy data files 112. While the example embodiment of FIG. 1 presents the identification module 128 as being separate and distinct from the service provider computer 102, in an alternative embodiment, the methodology, operations and/or computer-executable program instructions of the identification module 128 may be incorporated in whole or in part in the service provider computer, 102, the pharmacy computer 104, the claims processor computer 106, a separate processor driven device, or any combination thereof.

In certain example embodiments, the service provider computer 102 can further include or otherwise be in communication with an aggregation module 130. The aggregation module 130 can include computer-executable instructions operable for establishing an individual's patient medication history across one or more pharmacy entities and/or one or more claims processor entities without accessing patient medication history data corresponding to another individual. For example, the aggregation module 130 can establish an individual's patient medication history based at least in part on the linking indexes.

The aggregation module 130 can access the database 108 to retrieve linking indexes generated by identification module 128. As explained in detail below, the aggregation module 130 can use the keys in the linking indexes to link a single individual's patient medication history data records across one or more pharmacies/pharmacy computers 104 and one or more the claims processors/claims processor computers 106, without accessing patient medication history data for another individual. In one example embodiment, the service provider computer 102 can transmit the individual longitudinal identifiers (or another unique representation thereof) linked with the linking indexes for an individual to the pharmacy computer 104, the claims processor computer 106, or a third-party computer to allow for the respective computers to establish an individual's longitudinal medication history. In some such embodiments, the pharmacy computer 104, the claims processor computer 106 and/or the third-party computer can be in communication with the aggregation module 130 and can be in communication with the database 108. While the example embodiment of FIG. 1 presents the aggregation module 130 as being separate and distinct from the service provider computer 102, in an alternative embodiment, the methodology, operations and/or computer-executable program instructions of the aggregation module 130 may be incorporated, in whole or in part, in the service provider computer, 102, the pharmacy computer 104, the claims processor computer 106, a separate processor-driven device, or any combination thereof.

The network 132 may include any telecommunication and/or data network, whether public, private, or a combination thereof, including a local area network, a wide area network, an intranet, the Internet, intermediate handheld data transfer devices, and/or any combination thereof and may be wired and/or wireless, or any combination thereof. The network 132 may also allow for real time, offline, and/or batch transactions to be transmitted between or among the service provider computer 102, the pharmacy computer 104, and the claims processor computer 106. Various methodologies as described herein, may be practiced in the context of distributed computing environments. Although the service provider computer 102 is shown for simplicity as being in communication with the pharmacy computer 104, or the claims processor computer 106 via one intervening network 132, it is to be understood that any other network configurations are possible. For example, intervening network 132 may include a plurality of networks, each with devices such as gateways and routers for providing connectivity between or among the components of the system 100. Instead of or in addition to the network 132, dedicated communication links may be used to connect various devices in accordance with an example embodiment. For example, the service provider computer 102 may form the basis of network 132 that interconnects the pharmacy computer 104 and the claims processor computer 106.

Those of ordinary skill in the art will appreciate that the system 100 shown in and described with respect to FIG. 1 is provided by way of example only. Numerous other operating environments, system architectures, and device and network configurations are possible. Other system embodiments can include fewer or greater numbers of components and may incorporate some or all of the functionality described with respect to the system components shown in FIG. 1. For example, in an exemplary embodiment, the service provider computer 102 (or other computer) may be implemented as a specialized processing machine that includes hardware and/or software for performing the methods described herein. In addition, at least a portion of the processor 133 and/or the processing capabilities of the service provider computer 102, the claims processor module 150, and/or the pharmacy module 152, may be implemented as part of a pharmacy computer 104, the claims processor computer 106, third-party computer, or any combination thereof. Accordingly, embodiments of the disclosure should not be construed as being limited to any particular operating environment, system architecture, or device or network configuration.

Operational Overview

Certain portions of the exemplary methods discussed below will be described with reference to establishing an individual's patient longitudinal medication history, across a pharmacy and a plurality of the claims processors. However, this is only for purposes of example as the person of ordinary skill in the art would know how to establish an individual's patient longitudinal medication history over any combination of pharmacies and claims processors, based upon the teachings herein.

Figure 2:
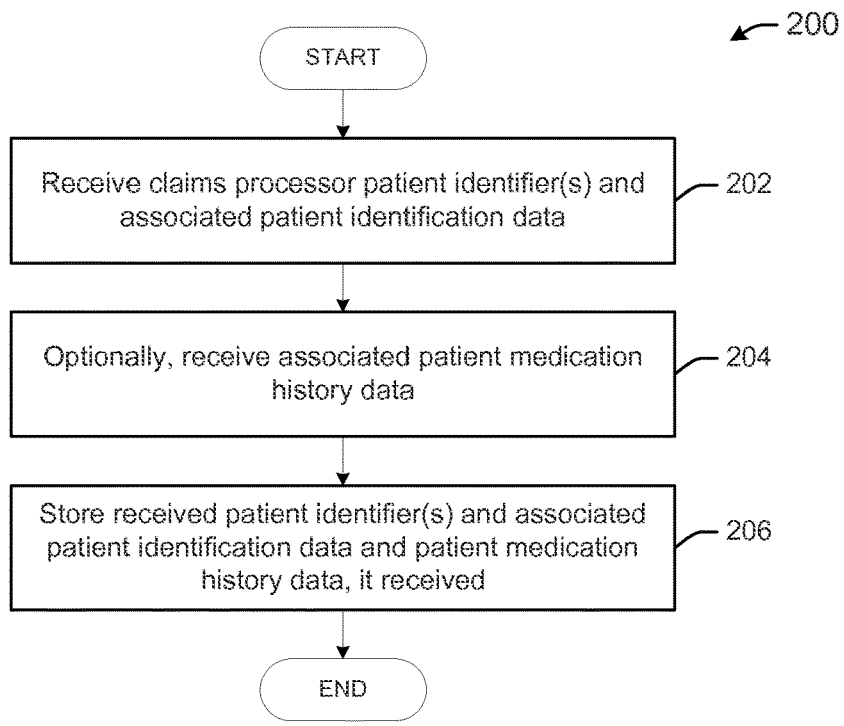
FIG. 2 is a flow chart illustrating an exemplary method for receiving an adjudicator patient identifier, patient identification data, and optional patient medication history data from an claims processor computer and for storing the received data, in accordance with one example embodiment of the disclosure.

FIG. 2 is a flow chart illustrating an exemplary method 200 for receiving a claims processor patient identifier, patient identification data, and optional patient medication history data from the claims processor (the claims processor computer(s) 106) and for storing the received data in the database 108.

Referring now to FIGS. 1 and 2, the exemplary method 200 begins at the START step and proceeds to step 202, where the claims processor computer 106 communicates, for one or more patients, a claims processor ID, and claims processor patient identifier and associated patient identification data from the claims processor computer 106 to the service provider computer 102. In certain example embodiments, the information can be communicated in response to the claims processor computer 106 signing-up for Eligibility Services performed by the service provider computer 102. For example, in order to start performing Eligibility Services for patients on behalf of claims processor computer 106, service provider computer 102 takes as input medication plans eligible patient listings received from claims processor computer 106 (or from one or more computer associated with any entity transacting through service provider computer as described above). The patient listings can include patient identification data along with a claims processor patient identifier for each patient. The claims processor patient identifier can be a unique identifier that can be used by the claims processor computer 106 to identify a patient's identification data and/or medication history data within the processor computer 106's own data files (e.g., data files 176). For example, using the claims processor patient identifier, the claims processor computer 106 can locate, update and/or retrieve the corresponding patient's identification data and/or patient medication history data in processor computer 106's own data files. In some example embodiments, a claims processor patient identifier can include, but is not limited to a numeric, an alphanumeric, or an alphabetical sequence of characters generated by the claims processor computer 106. In some example embodiments, a claims processor patient identifier can include, but is not limited to, a HICN or social security number. In some example embodiments, the claims processor ID can be an identifier that is used by service provider computer 102 to uniquely identify different claims processors/claim processor computer(s) 106. In some example embodiments, the claims processor ID can be a numeric, an alphanumeric, or an alphabetical sequence of characters generated by claims processor computer 106. In other example embodiments, the claims processor ID can include, but is not limited to a BIN, PCN, Group ID or combination thereof. In certain example embodiments, the identification module 128 or another portion of the service provider computer 102 receives the claims processor patient identifier, claims processor ID and associated patient identification data from the claims processor computer 106 via the network 132.

At step 204, the service provider computer 102 optionally retrieves patient medication history data linked with the claims processor patient identifier from the patient medication history data files 118, if provided to the database 108 by the claims processor computer 106. In some example embodiments, the claims processor computer 106 can communicate patient medication history data linked with the claims processor patient identifier to database 108 for storage in the database 108, or to the service provider computer 102 for storage in the database 108. Upon receiving an eligibility request from the pharmacy computer 104 (and/or from a third party computer), the service provider computer 102 can retrieve patient medication data for the request from database 108 on behalf of claims processor computer 106. For other Eligibility services, service provider computer 102 can provide the service to claims processor computer 106 without receiving patient medication history data.

In one exemplary embodiment, the claims processor management module 124 can access the claims processor patient identifier, claims processor ID, patient identification data, and optional patient medication history data stored in data files 176 or another database and communicate that data to the claims processor module 150, identification module 128 or another portion of the service provider computer 102. For example where the identification module 128 is a part of the service provider computer 102 or otherwise affiliated with the service provider computer 102, the delivery of the claims processor patient identifier, claims processor ID, patient identification data, and optional patient medication history can be an internal delivery or an intra-network delivery. However, where the claims processor module 150 is a processor-based system distinct from the service provider computer 102, the delivery of the claims processor patient identifier, patient identification data, and optional patient medication history data may be an external delivery, for example, via the network 132, according to an example embodiment of the disclosure.

At step 206, the service provider computer 102 stores the claims processor patient identifier, claims processor ID and received patient identification data in, for example, the database 108. If the medication history data is also received, this data can also be stored in the database 108. The service provider computer 102 can store the received claims processor patient identifier, claims processor ID and patient identification data in the patient identification data files 116 and optional patient medication history data in the patient medication history data files 118 in the database 108. In some example embodiments, the service provider computer 102 can link the claims processor patient identifier to the claims processor ID, patient identification data and optional patient medication history data in the database 108. In such embodiments, the service provider computer 102 can locate, update and/or retrieve a claims processor's patient identification data and optional patient medication history data in database 108 using the claims processor patient identifier received from the claims processor computer 106. In some exemplary embodiments, to facilitate later processing of received patient identification data (e.g., by method 300), service provider can keep a record of newly received patient identification data that is stored in patient identification data files 116. In some such embodiments, newly received patient identification data can be stored in a data structure including a flag to indicate that it is newly received. For example, newly received patient identification data can be stored in a database structure (along with previously received patient identification data) where a row (or column) contains a database field for a flag. In some embodiments, the flag can be an integer, such as a "1" to indicate newly received patient identification data and/or a "0" to indication previously received patient identification data or a date and time stamp to indicate the time or receipt or time of transmission. The method then proceeds to the END step.

In certain example embodiments of method 200, prior to starting at step 202, the database 108 may have previously stored the claims processor patient identifiers, linked patient identification data and, linked optional patient medication history data received from the claims processor computer 106. In some such embodiments, service provider computer can access database 108 to determine if any of the stored claims processor patient identifiers match a claims processor patient identifier received at step 202. If not the service provider computer 102 can store the claims processor patient identifier received at step 202 in the database 108, patient identification data received at step 202 in patient identification data files 116 and, if received, patient medication history data received at step 204 in patient medication data files 118. If so, the service provider computer 102 can compare the newly received patient identification data at step 202 with the patient identification data patient identification data files 116 and linked with the claims processor patient identifier. If the newly received patient identification data at step 202 is the same as the patient identification data stored in patient identification data files 116, the service provider computer 102 can store the optional patient medication history data, if received at step 204, in patient medication history data files 118 and link it with the stored claims processor patient identifier. If the newly received patient identification data at step 202 is not the same as patient identification data stored in patient identification data files 116, the service provider computer 102 can store, in the patient identification data files 116, the newly received patient identification data and, if received at step 204, the newly received patient medication history data in the patient medication history data files 118, and link the newly stored data with the corresponding stored claims processor patient identifier.

Figure 3:
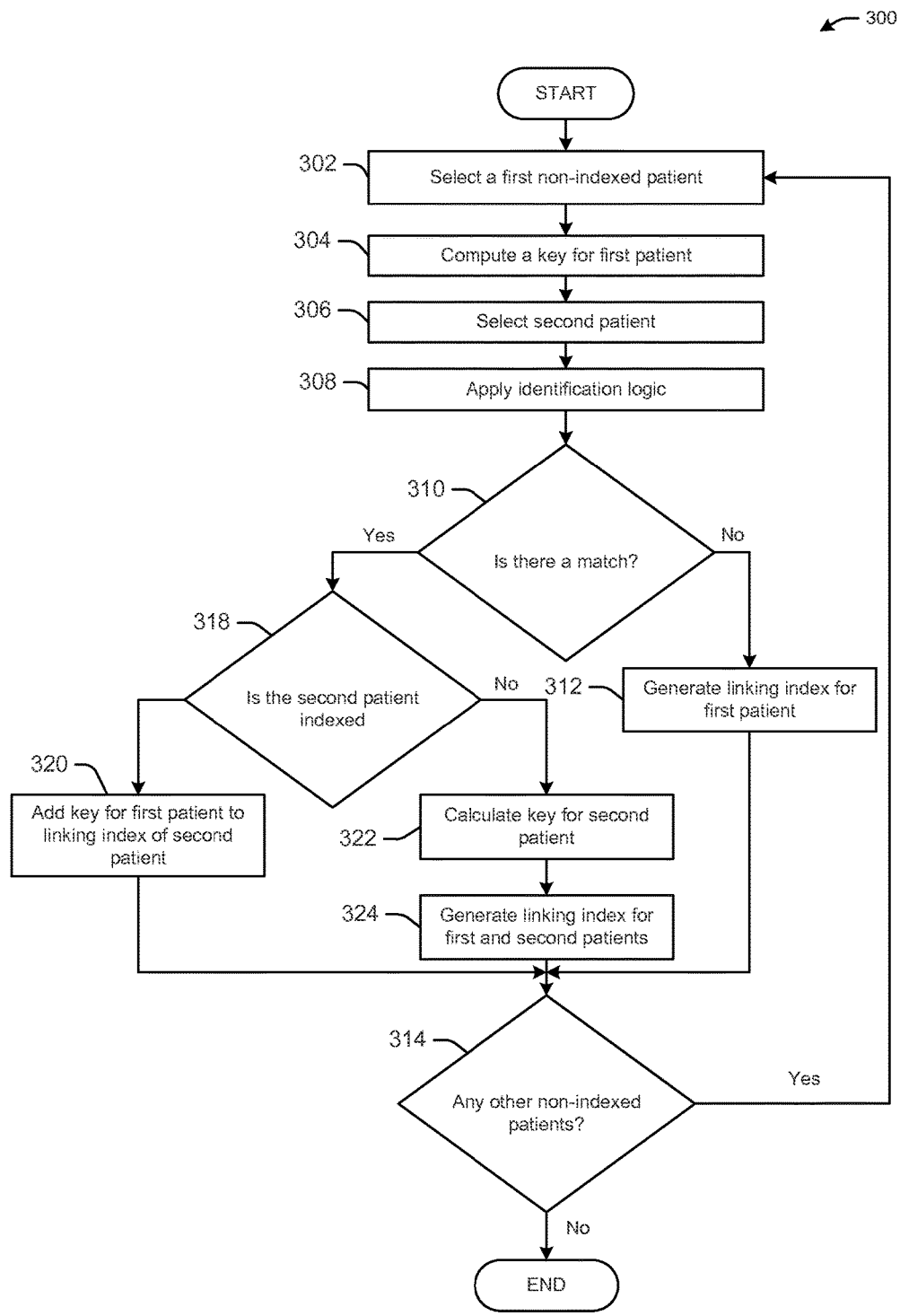
FIG. 3 is a flow chart illustrating an exemplary method for generating and/or updating a linking index based at least in part on stored patient identification data received from multiple claims processor computers, in accordance with one example embodiment of the disclosure.

FIG. 3 is a flow chart illustrating an exemplary method 300 for generating and/or updating a linking index based, at least in part, on the patient identification data 116 stored in the database 108 and received from multiple claims processors (the claims processor computer(s) 106) according to one example embodiment of the disclosure. Referring now to FIGS. 1 and 3, the exemplary method 300 begins at the START step and proceeds to step 302. In some example embodiments, the method 300 can be performed at one or more preselected time intervals (e.g., hourly, daily, weekly, monthly, quarterly, or yearly) and/or upon the service provider computer 102 receiving an indication from a user to start method 300. In some example embodiments, the method 300 can be invoked independently of the method 200, where patient identification data and/or patient medication history data is received by the service provider computer 102 from the claims processor computer 106. Accordingly, in some such example embodiments, the patient identification data files 120 may contain patient identification data that has not been previously processed by the identification module 128 to generate a linking index or update a previously generated index. At step 302 the identification module 128 or another portion of the service provider computer 102 selects the patient identification data associated with a first patient (i.e., patient identification data associated with a claims processor patient identifier) that is not indexed. Patient identification data that is not indexed can refer to patient identification data that has not yet been processed by the identification 128 to generate or update a linking index (e.g., patient identification data that has not been processed by method of step 300). In one exemplary embodiment, the identification module 128 can select a non-indexed patient from the patient identification data files 116 by accessing database 108. In some example embodiments, the identification module 128 can determine if patient identification data has been indexed by determining the value of a flag linked to the patient identification data, as described above in the method 200. In general, in batch processing embodiments, where the patient identification data is previously stored by service processing computer 102, the non-indexed patient identification data can be randomly selected. In sequential processing embodiments, where the method 300 is performed as data is received (e.g., in method 400 described below), method 300 can be performed by identification module 128 as it is received by service provider computer 102.

Continuing to step 304, the identification module 128 or another portion of the service provider computer 102 computes a key for the first patient. A key can include one or more key fields and corresponding key values. The key fields are configurable based on the desires of the designer, can be preselected, and can be chosen from the patient identification data. In one example embodiment, a key can include the following key fields: patient date of birth|patient cardholder ID|patient person code|claims processor ID. The corresponding values can be the value of the key fields in the patient identification data. As is explained in detail below, the keys can be used to establish a patient's longitudinal medication history in accordance with patient privacy regulations.

At step 306, the identification module 128 or another portion of the service provider computer 102 selects patient identification data for a second patient from patient identification data files 116. In some example embodiments, the selection of patient identification data for a second patient is based at least in part on patient privacy regulations and the presence or absence of contractual relationships between different covered entities. For example, in the example embodiment depicted in FIG. 3, the covered entities are claims processors. Current patient privacy regulations permit distinct claims processors to share an individual's identification information without that individual's consent, but only within the context of a data rights management contract between the distinct claims processors and the service provider that allows service provider computer 102 to share patient identification data between claims processors that are signed up for eligibility services. Accordingly, in some example embodiments, patient identification module 128 can query contract data files 114 to identify which claims processors/claims processor computer 106 have a data rights management contract with the claims processor/claims processor computer 106 associated with the first patient. In such example embodiments, identification module 128 can select a second patient's identification from patient identification data files 116 associated with the identified claims processors/claims processor computer 106. In some example embodiments, where service provider computer 102 requires patient identification data sharing with service provider computer 102 as a term of service as described above, patient identification module 128 can select any patient identification data from patient identification data files 116 (i.e., there is a patient identification data files 116 are received on behalf of claims processors that have patient identification data sharing agreement between them).

Identification module 128 can select patient identification data for the second patient without regards to whether the patient identification data was previously indexed by identification module 128. In certain example embodiments, selection of the patient identification data corresponding to the second patient can be random. At step 308, the identification module 128, for example, applies identification logic to the patient identification data of the first and second patients to determine whether the first and second patients correspond to the same individual. In particular, the identification module 128 can compare the patient identification data corresponding to the first patient and the patient identification data corresponding to the second patient to determine if the patient identification data for both correspond to the same individual. In some example embodiment, the identification logic can apply probabilistic matching techniques to patient identification data to effect the comparison. In such example, embodiments, matching functions can be applied to preselected patient identification data elements ("match fields") obtained from the patient identification data associated with the first and second patients. A match field can include, but is not limited to, any patient identification data. In certain example embodiments, a match field can include patient first name, patient last name, patient date of birth, patient gender, patient address (or address EUID (normalized address), patient spouse's first name, patient spouse's last name, patient family count (e.g., number of family members covered by the patient's health insurance plan), patient address ID (address identifier used by the claims processor computer 106 to identify the patient's address).

The matching functions can be an exact matching function (i.e., returning first value if all of the input match fields are an exact match and returning a second value if even one of the input match fields are not an exact match) or a similarly matching function (i.e., return a spectrum of values based upon the similarity of the input match fields) and can be independently selected for each match field. The matching functions can be applied to corresponding match fields from the first and second patient to obtain matching values for each of the match fields. For example, if the match fields are represented by $D_1$, $D_2$ and $D_3$ and the matching functions are $f_1$, $f_2$, and $f_3$, the identification module 128 or another portion of the service provider computer 106 can compute match values $f_1(D_{1,1},D_{1,2})$, $f_2(D_{2,1},D_{2,2})$ and $f_3(D_{3,1},D_{3,2})$, where $D_{n,1}$ and $D_{n,2}$ correspond to the values of match fields $D_n$, obtained from the patient identification information for patients 1 and 2, respectively. As a further example, $D_1$ and $D_2$ can correspond to "patient first name" and "patient last name", respectively. In such an example, match values $f_1$ ("patient first name" of patient 1, "patient first name" of patient 2) and $f_2$ ("patient last name" of patient 1, "patient last name" of patient 2) can be computed. The identification module 128 can calculate an overall matching score based upon the computed match values and determine if the overall matching score meets or exceeds a threshold value. In some example embodiments, each match value can be independently weighted in the calculation of the overall matching score. For example, match values $f_1(D_{1,1},D_{1,2})$, $f_2(D_{2,1},D_{2,2})$ and $f_3(D_{3,1},D_{3,2})$ can have corresponding weights $w_1$, $w_2$ and $w_3$ such that the quantities $w_1 f_1(D_{1,1},D_{1,2})$, $w_2 f_2(D_{2,1},D_{2,2})$ and $w_3 f_3(D_{3,1},D_{3,2})$ are used in calculating the overall matching score.

In step 310, an inquiry is conducted to determine if a match exists (e.g., the first and second patients correspond to the same individual). In one example embodiment, this determination can be made by the identification module 128 or another portion of the service provider computer. If the identification module 128 determines the threshold value is exceeded or met or exceeded by the overall matching score, the identification module 128 can determine that the first and second patients correspond to the same individual and the YES branch is followed to step 318. If the identification module 128 determines that the threshold value is not exceeded or not met or exceeded by the overall matching score, the identification module 128 determines the first and second patients correspond to different individuals and the NO branch is followed to step 312. In other example embodiments, the identification module 128 can incorporate a threshold range. For example, identification module 128 can use an upper threshold value and a lower threshold value to define a threshold range of values. In such example embodiments, if the upper threshold value is exceeded or met or exceeded by the overall matching score, the identification module 128 can determine that the first and second patients correspond to the same individual. If the identification module 128 determines that the lower threshold value is not exceeded or not met or exceeded by the overall matching score, the identification module 128 determines the first and second patients correspond to different individuals. If the identification module 128 determines that the overall matching score is between the upper threshold value and lower threshold value, identification module 128 can invoke exception logic. In one example embodiment, exception logic can request a user to manually review the patient identification for the first and second patient and make a manual determination whether the patient identification data for the first and second patient correspond to the same individual.

At step 312, the identification module 128 creates a linking index for the individual represented by the identification data corresponding to the first patient. In certain example embodiments, a linking index can include one or more patient keys and one or more claims processor IDs. In some such example embodiments, the keys can be linked with the claims processor ID corresponding to the patient identification data upon which the key was computed. For example, in some example embodiments, if a key is computed from patient identification data provided by claims processor A to service provider computer 102, the linking index can link the key with the claims processor ID for claims processor A. In some example embodiments, a linking index can directly or indirectly include the claims processor IDs. For example, at step 312 the linking index can include a data structure with the key of the first patient in a row and the claims processor ID in the same row, in a column preceding or following the columns containing the key. In some example embodiments, the key can include the claims processor ID corresponding to the patient identification data upon which the key was computed. In some example embodiments, the linking index can include an individual longitudinal identifier, as described above. The individual longitudinal identifier can be used by aggregation module 130, as described below in the method 700, to identify linking indexes corresponding to an individual. In some example embodiments, identification module 128 or another portion of the service provider computer 102 can communicate the linking index to the database 108 and store the linking index therein. In some such embodiments, the linking index can be stored in the claims processor data files 110. Following creation of the linking index, the method continues to step 314, where an inquiry is conducted to determine if there are any other non-indexed patients in the patient identification data files 116. In one example embodiment, the determination is made by the identification module 128 or another portion of the service provider computer 102. For example, the identification module 128 can determine whether there are any other patients (i.e., patient identification data associated with the claims processor ID) in the patient identification data files 116 that are not indexed. If there are other patients that are not indexed, then the YES branch is followed and the method returns to step 302. If there are no other patients that are not indexed, then the NO branch is followed to the END step.

At step 318, the identification module 128 or another portion of the service provider computer 102 determines if the patient identification data for the second patient is indexed, as described above. In one example embodiment, the identification module 128 or another portion of the service provider computer 102 determines whether the second patient is indexed. If the second patient is not indexed, the NO branch is followed and the method continues to step 322. If the second patient is indexed, the YES branch is followed and the method continues to step 320. At step 320, the identification module 128 adds the key for the first patient to the linking index including the second patient's key (e.g., determines the patient identification data for the first and second patient correspond to the same individual). The method then proceeds to step 314, described above.

At step 322, the identification module 128 or another portion of the service provider computer 102 calculates a key for the second patient. In some example embodiments, the key fields have one or more key fields in common with the first patient's key. For example, the key fields can have one, more than one, or all key fields in common. In step 324, the identification module 128 creates a linking index that includes the first patient's key and the second patient's key. As described above, the linking index can include the claims processor patient identifiers for the first patient's key and the second patient's key. Also as described above, the linking index can also include an individual longitudinal identifier. In one example embodiment, the identification module 128 can store the linking index in the claims processor data files 110. Following creation of the linking index, the method continues to step 314, which is described in detail above.

Figure 4:
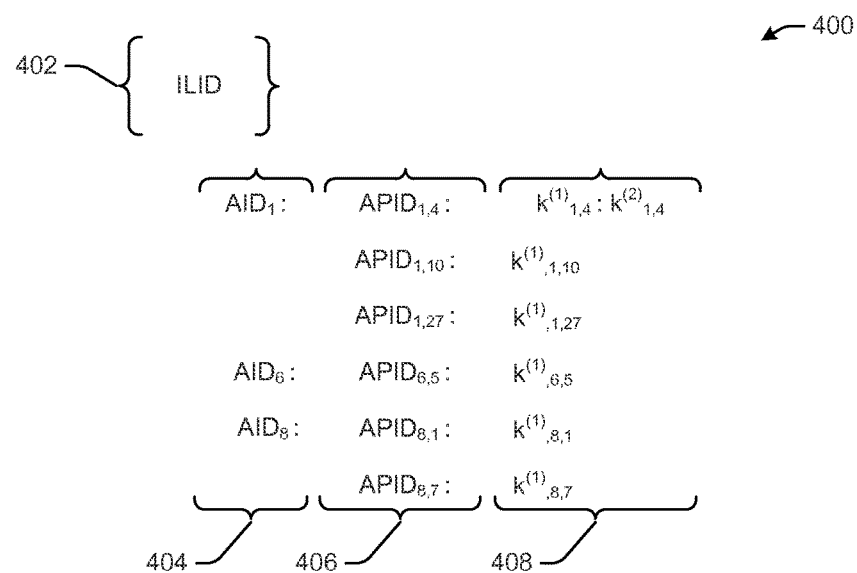
FIG. 4 is a schematic representation of one embodiment of a linking index generated from patient identification data received from multiple claims processor computers, in accordance with one example embodiment of the disclosure.

FIG. 4 is a schematic representation of one example embodiment of a linking index 400 generated from patient identification data received from multiple claims processor computers 106 according to one example embodiment of the disclosure. For example, the linking index represented in FIG. 4 can be generated by the exemplary method described in FIG. 3. Referring to FIG. 4, the linking index 400 is linked with the individual longitudinal identifier ILID 402. The exemplary linking index 400 includes claims processor IDs 404, corresponding claims processor patient identifiers 406 and corresponding keys 408. In FIG. 4, $AID_n$ refers to the claims processor ID associated with the claims processor n/claims computer n. $APID_{n,m}$ refers to the claims processor patient identifier used by the claims processor computer n to uniquely identify patient m's patient identification data and/or patient medication history data in the claims processor data files 110 and/or in the data files 176. $k_{n,m}^{(1)}$ refers to a first key computed for patient m of the claims processor computer n. For example, $k_{n,m}^{(1)}$ refers to the first key computed on the patient identification data associated with patient m of the claims processor computer n. In one example, $AID_n$ can be incorporated into the corresponding key, instead of a separate element in the linking index (e.g., the claims processor ID can be a preselected key field in the keys).

Figure 5:
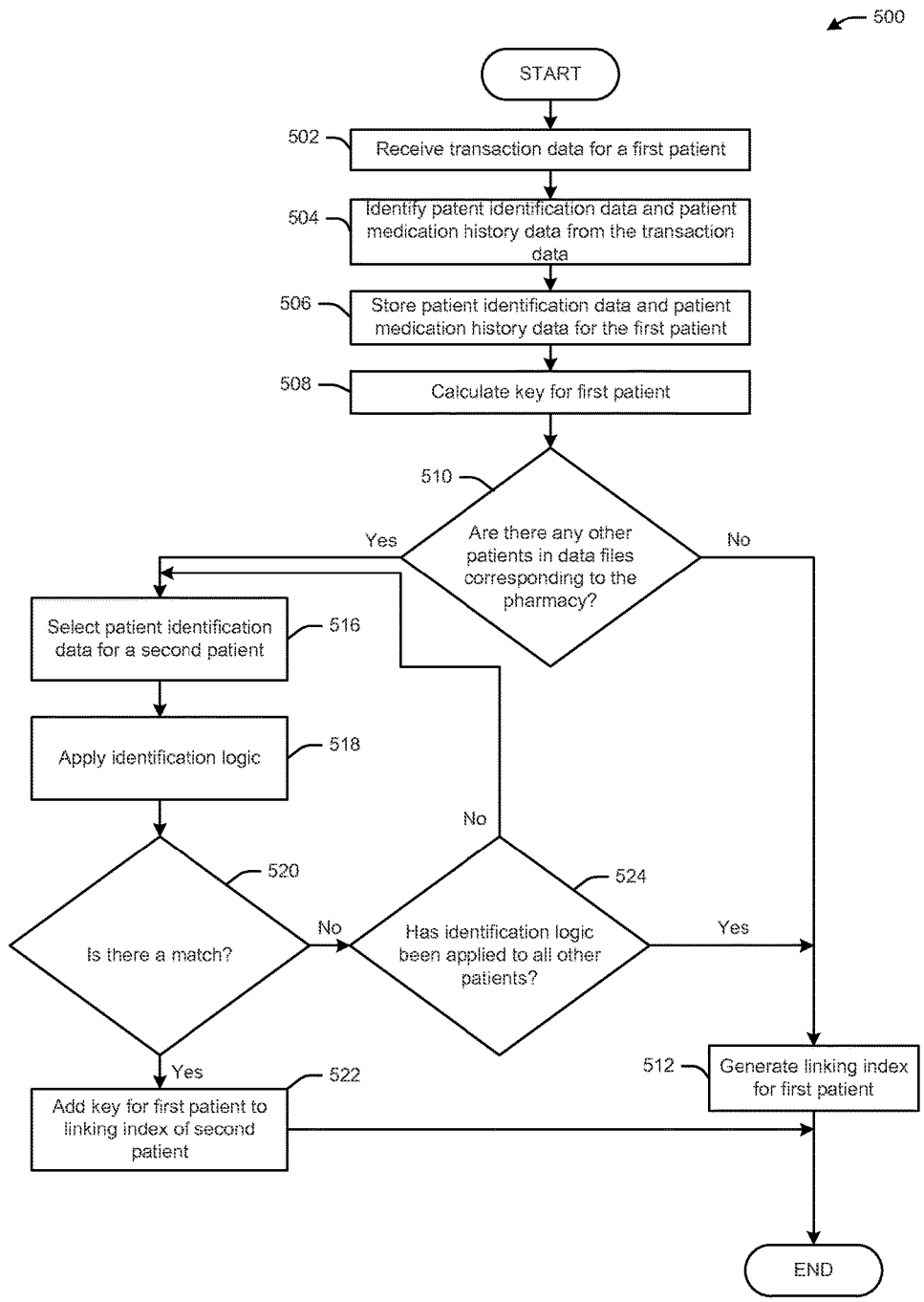
FIG. 5 is a flow chart illustrating an exemplary method for receiving and storing patient identification data and patient medication history data received from a pharmacy and for generating or updating a linking index based at least in part on the received data, in accordance with one example embodiment of the disclosure.

FIG. 5 is a flow chart illustrating an exemplary method 500 for receiving and storing patient identification data and patient medication history data received from a pharmacy (pharmacy computer(s) 104) and for generating or updating a linking index based at least in part on the received data according to one example embodiment of the disclosure. Referring to FIGS. 1 and 5, the exemplary method 500 begins at step 502, where the identification module 128 or another portion of the service provider computer 102 receives healthcare transaction data for a first patient from a pharmacy computer 104 corresponding to a pharmacy as part of a healthcare transaction (e.g., predetermination of benefits transactions, X-12 270/271 eligibility verification requests, healthcare claim transactions, prescription claim or billing requests, healthcare order transactions, or e-prescription transactions (i.e., electronic prescription order transactions, e-scripts, or e-prescriptions)). The healthcare transaction data can include patient identification data and patient medication history data. At step 504, the identification module 128 parses the healthcare transaction and identifies all or a portion of the patient identification data (described above) and patient medication history data (described above) from the transaction data in the healthcare transaction. In certain example embodiments, the patient identification data received in the transaction data can include, but is not limited to, patient first name, patient last name, patient date of birth, patient address (street address, city, state, zip/postal code), patient gender, patient cardholder ID, prescriber NPI, or claims processor ID.

At step 506, the identification module 128 or another portion of the service provider computer stores the identified patient identification data and patient medication history data and associates them. In some example embodiments, the identification module 128 stores the identified patient identification data in the pharmacy identification data files 120 and the identified patient medication history data in the pharmacy medication history data files 122 of the database 108. In one example, the pharmacy identification data files 120 and the pharmacy medication history data files 122 can be localized (i.e., the pharmacy identification data files and the pharmacy medication history data files from different pharmacies are stored separately for each pharmacy so that the data from different pharmacies is not commingled).

At step 508, the identification module 128 can compute a key from the received patient identification data, as described above in step 304 of FIG. 3. In some embodiments, the key can be represented by the following key fields: patient date of birth|patient cardholder ID|patient person code|claims processor ID, and can have corresponding key values. At step 510, identification module 128, which can access the pharmacy data files 112 associated with the pharmacy/pharmacy computer 104 to determine whether there is patient identification data for any other patients (i.e., identification module 128 determines if the service provider computer 102 had, prior to receiving the healthcare transaction data for the first patient, received and stored healthcare transaction data from the pharmacy computer 104). In one example embodiment, where pharmacy data files 112 include patient identification data for more than one pharmacy, the identification module 128 can identify patient identification data for a given pharmacy using the NPI number associated with the transaction. If so, the YES branch is followed and the method continues to step 516. Otherwise, the NO branch is followed to step 512.

At step 512, the identification module 128 creates a linking index for the first patient (i.e., the identification module 128 has recognized the first patient as a unique individual with respect to the first pharmacy entity/pharmacy computer 104). In some example embodiments, the linking index can include one or more patient keys. For example, at step 312 the linking index can include the key of the first patient. In some such embodiments, a linking index can further include a pharmacy ID (e.g., NPI number, chain identifier, store number, etc.) associated with the pharmacy computer 104 from which the patient identification data was received by the identification module 128 and/or the service provider computer 102. The pharmacy ID can be an identifier, relative to the service provider computer 102, that uniquely identifies a pharmacy and/or a pharmacy store, as described further below. In one example embodiment, the identification module 128 can also generate a unique individual longitudinal identifier that uniquely identifies, relative to the service provider computer 102, the linking index (and the corresponding individual). The linking index can include or otherwise be associated with the individual longitudinal identifier. For example, the identification module 128 or another portion of the service provider computer 102 can use the unique individual longitudinal identifier to identify the linking index corresponding to an individual. The identification module 128 can communicate the linking index to the database 108 and store the linking index therein. For example, the linking index can be stored in with the pharmacy data files 112. The method then proceeds to the END step.

At step 516, the identification module 128 selects patient identification data for a second patient, distinct from the first patient. In some example embodiments, identification module 128 can randomly select patient identification from pharmacy data files 112. In other example embodiments, identification module 128 can sequentially access patient identification data records, skipping the patient identification data for the first patient. At step 518, the identification module 128 applies identification logic, described above with respect to FIG. 4, to determine whether the patient identification data corresponding to the first and second patients correspond to the same individual. In one example, match fields for patient matching can include, but are not limited to, a patient first name, a patient last name, a patient date of birth, a patient gender, a patient cardholder ID, a patient address, a prescriber NPI, or an claims processor ID. At step 520, an inquiry is conducted to determine if the patient identification data for the first patient matches that of the second patient, thereby identifying the same, singular individual. In one example embodiment, the determination is made by the identification module 128 or another portion of the service provider computer 102. For example, the identification module 128 can determine, based upon an overall matching score and a preselected threshold value, whether the patient identification data corresponding to the first and second patient correspond to the same individual (as described above with respect to step 310 of the method 300). If not, the NO branch is followed and the method continues to step 524 (i.e., the identification module 128 determines that the patient identification data for the first and second patients correspond to different individuals). On the other hand, if the identification module 128 determines that the patient identification data of the first and second patients correspond to the same individual, then the YES branch is followed to step 522.

At step 522, the key calculated for the first patient is added to the linking index that includes the second patient's key. In certain example embodiments, the linking index that includes the second patient's key can include a individual longitudinal identifier as described above in step 312 of the method 300 and further below in method 700. In some such embodiments, the identification module 128 can associate the unique identifier with the patient identification data and/or patient medication history data for the first patient stored in the pharmacy data files 112. The method then proceeds to the END step.

At step 524, an inquiry is conducted to determine if the matching logic has been applied to all other patient identification data. In one example embodiment, the determination is made by the identification module 128 or another portion of the service provider computer 102, which determines if the matching logic has been applied between the patient identification data of the first patient and all other patients in the pharmacy data files 112. In one such exemplary embodiment, identification module 128 or another portion of the service provider computer 102 can sequentially access patient identification data records in patient identification data files 120 at step 516 and, at step 524, can determine if the end of patient identification data records has been reached. If matching logic has not been applied between the patient identification data of the first patient all other patients in the pharmacy data files 112, the YES branch is followed and the method proceeds to step 512. If so, the NO branch is followed and the method returns to step 516 to attempt to apply matching logic to the patient identification data files in the pharmacy data files 112 corresponding to another patient.

Figure 6:
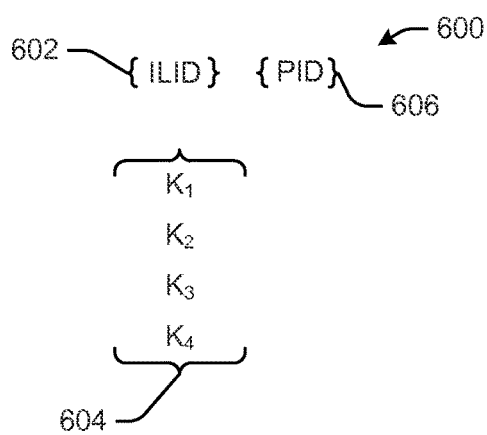
FIG. 6 is a schematic representation of a linking index generated from patient identification data received from a pharmacy, in accordance with one example embodiment of the disclosure.

FIG. 6 is a schematic representation of a linking index generated from patient identification data received from a pharmacy/pharmacy computer 104. For example, the linking index represented in FIG. 6 can be generated by the method in FIG. 5. The exemplary linking index 600 includes a individual longitudinal identifier 602 and four keys ($K_1$-$K_4$) 604. Keys $K_1$-$K_4$ can independently correspond to an individual's patient identification data as represented by the pharmacy/pharmacy computer 104. For example, exemplary linking index 600 and $K_1$ can be initially generated at step 512 from an individual's patient identification data. Continuing with the example, $K_2$-$K_4$ can be added to the exemplary linking index 600 containing $K_2$-$K_4$ can at step 522 from distinct patient identification data corresponding to the same individual. The exemplary linking index 600 further includes a pharmacy ID 606 ("PID") that uniquely identifies the pharmacy/pharmacy computer 104 corresponding to the patient identification data upon which the keys in linking index 600 were computed. In some exemplary embodiments, a pharmacy ID can include, but is not limited to, an alphabetical, numerical or an alphanumeric sequence of characters. In some exemplary embodiments, a pharmacy ID can include, but is not limited to, a pharmacy store identifier (e.g., an NPI number), a pharmacy chain identifier, or a combination thereof.

Figure 7:
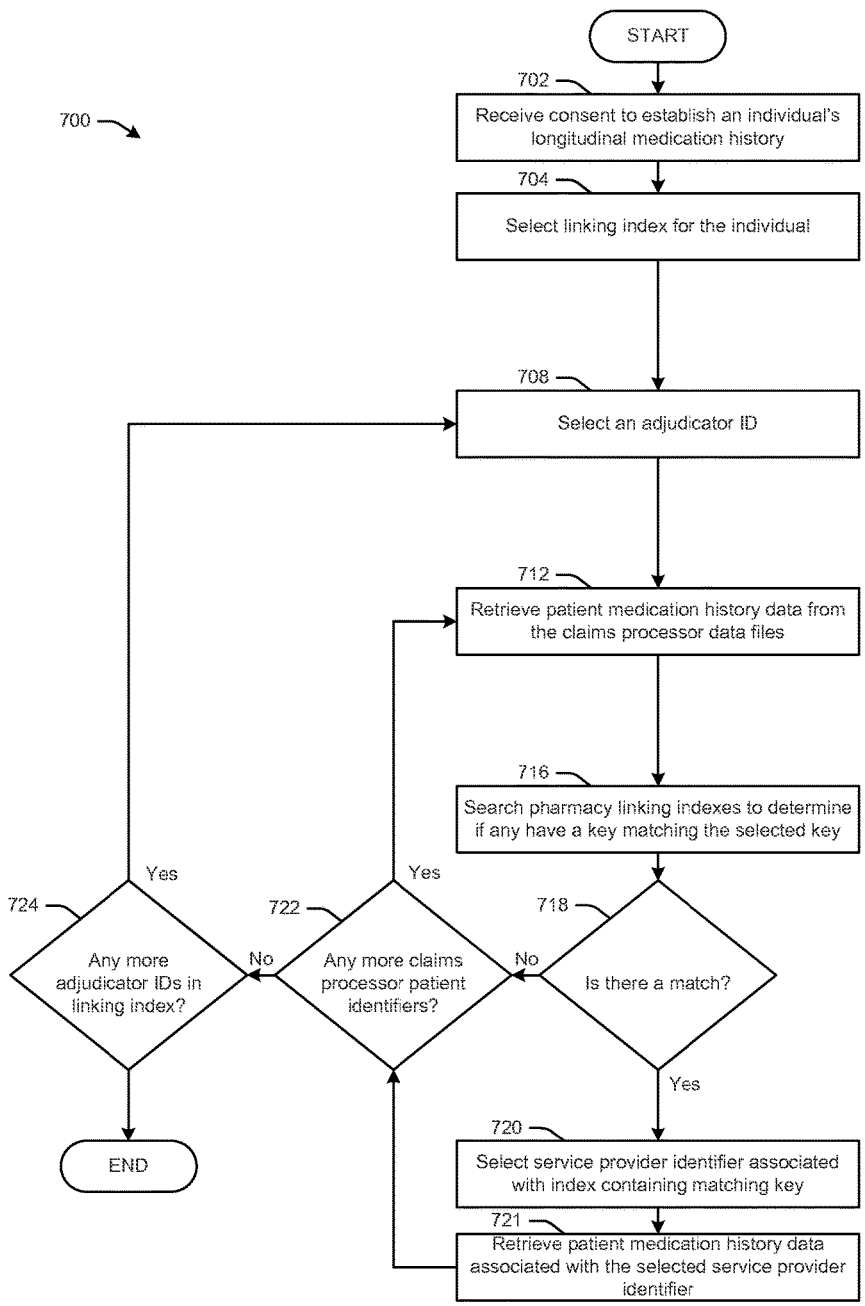
FIG. 7 is a flow chart illustrating an exemplary method for establishing an individual's longitudinal medication history across a pharmacy and multiple claims processor computers, in accordance with one example embodiment of the disclosure.

FIG. 7 is a flow chart illustrating an exemplary method 700 for generating an individual's longitudinal medication history across a selected pharmacy and a selected set of claims processors. The example method 700 can establish an individual's longitudinal medication history without accessing patient identification data or patient medication history data associated with other individuals. Referring to FIGS. 1, 4, and 7, the method 700 begins at the START step and proceeds to step 702, where the aggregation module 130 or another portion of the service provider computer 102 receives consent, on behalf of an individual, to establish the individual's longitudinal medication history across a given pharmacy and multiple claims processors. The patient consent can be in the form of a communication from the pharmacy computer 104, the claims processor computer 106 or another third-party computer (i.e., a computer other than service provider computer 102, the pharmacy computer 104 or the claims processor computer 106) that an individual consents to having the service provider computer 102 generate the individual's patient medication history from the patient medication history data files associated with the pharmacy and patient medication history data files associated with each of the multitude of claims processors for which data is available for the particular individual/patient. For example, consent can be in the form of a communication from a third-party computer that a patient has consented to the third-party computer generating the patient's longitudinal medication history. The patient consent can include, or the service provider computer can identify from a table in data files 140, the pharmacy identifier corresponding to the selected pharmacy and the claims processor IDs corresponding to the selected set of claims processors. After receiving consent, the method continues to step 704.

At step 704, the aggregation module 130 or another portion of the service provider computer 102 selects a linking index corresponding to the individual. In some example embodiments, the aggregation module 130 can receive, from claims processor computer 106, patient identification data corresponding to an individual along with receiving the individual's indication of consent. In some such exemplary embodiments, aggregation module 130 can compute a key from the patient identification data, for example, as described above at step 304 in the method 300. Aggregation module 130 or another portion of the service provider computer 102 can parse the linking indexes stored in claims processor data file 110 and identify a linking index having a matching key and a claims processor ID associated with one of the claims processors in the selected set of claims processors. One example embodiment of a claims processor linking index is shown in FIG. 4. Referring to FIGS. 4 and 7, in one example embodiment, service provider computer 102 receives an individual's consent to generate the individual's patient medication history over a selected set of claims processors including $AID_1$. In such an example, aggregation module 130 can compute a key matching $k_{1,4}^{(1)}$ at step 704 and select exemplary key index 400 linked with $AID_1$. At step 708, the aggregation module 130 can parse the selected linking index and identify and select a claims processor patient identifier linked with the matching key. For example, referring to FIG. 4, the aggregation module 130 can identify $APID_1$ as the claims processor patient identifier linked with $k_{1,4}^{(1)}$. At step 712, the aggregation module 130 or another portion of the service provider computer 102 can use the identified claims processor patient ID to access the claims processor data files 110 in the database 108 and/or data files 176 in the claims processor computer 106 and retrieve patient medication history associated with the identified claims processor patient identifier.

At step 716, the aggregation module 130 can access the pharmacy data files 112 in the database 108 to find key indexes having keys matching the key computed in step 704 and a pharmacy ID associated with the selected pharmacy and/or pharmacy store. In one example embodiment, the matching can include determining if the selected key is identical to one or more keys identified in the pharmacy data files 112. For example, referring to FIGS. 4 and 6, if $k_{1,4}^{(1)}$ is represented by the key fields: (patient date of birth|cardholder ID|person code|claims processor ID) with the corresponding key values (Jan. 1, 1980|12345678|02|5) and $K_2$ is represented by the key fields (patient date of birth|cardholder ID|person code|claims processor ID) with the corresponding key values (Jan. 1, 1980|12345678|02|5), the aggregation module 130 would determine that $k_{1,4}^{(1)}$ and $K_2$ match. Continuing with the example, if $k_{1,4}^{(1)}$ and $K_2$ had at least one key value that differed between the corresponding key fields, the aggregation module 130 would determine that $k_{1,4}^{(1)}$ and $K_2$ did not match. In an alternative embodiment, probabilistic matching techniques, as described above at step 310 of FIG. 3 can be used to determine if two keys match. In this alternative embodiment, the fact that one or more key values for corresponding key fields in two different keys do not match is not dispositive of whether a match does or does not exist. Instead, that determination is based on the values assigned to each key field, the overall score of the probabilistic matching evaluation and the comparison of that score to a threshold score to determine if a match does or does not exist.

In step 718, an inquiry is conducted to determine if a matching key was identified. In one example embodiment, the determination can be made by the aggregation module 130 or another portion of the service provider computer 102. If a matching key was identified, the YES branch is followed to step 720. Otherwise, the NO branch is followed to step 722. At step 720, the aggregation module 130 or another portion of the service provider computer 102 selects the individual longitudinal identifier linked with the pharmacy linking index comprising the matching key. Returning to the previous example, and referring to FIG. 6, aggregation module 130 would select ILID. At step 721, the aggregation module accesses the pharmacy data files 112 and retrieves the patient medication history data associated with the matching key. At step 722, an inquiry is conducted to determine if any additional claims processor patient identifiers are associated with the claims processor ID in the selected claims processor linking index. In one example embodiment, the determination can be made by the aggregation module 130 or another portion of the service provider computer 102. Returning to the previous example and referring to FIG. 4, aggregation module 130 can select $APID_{1,10}$. If it is determined that there are additional claims processor patient identifiers associated with the claims processor ID, then the YES branch is followed and the method returns to step 712. Otherwise, the NO branch is followed to step 724.

At step 724, an inquiry is conducted to determine if there are any additional claims processor IDs in the selected claims processor linking index. In certain example embodiments, the determination is made by the aggregation module 130 or another portion of the service provider computer 102. In one example embodiment, the aggregation module 130 determines if there are additional claims processor IDs by parsing the linking index selected at step 704. If there are claims processor IDs, the YES branch is followed and the method returns to step 708. On the other hand, if there are no additional claims processor IDs in the selected claims processor linking index, then the NO branch is followed to the END step. In certain example embodiments, the service provider computer 102 can send the retrieved data to the pharmacy computer 104, the claims processor computer 106, and/or a third-party computer. In some example embodiments, service provider computer can perform post-processing on the patient medication history data following agglomeration, for example, as describe in method 700. For example, the agglomerated data can be de-duped (e.g., a duplicate medication history data can be removed).

While method 700 describes agglomeration of patient medication history data across a plurality of claims processors and a single pharmacy, a person of ordinary skill in the art will be able to agglomerate patient medication history over any combination of one or more pharmacy stores, one or more pharmacies and/or one or more claims processors, based upon the teachings herein. For example, identification module 128 can create a distinct linking index for each individual over each claims processor/claims processor computer 106, over each pharmacy/pharmacy computer 104, and/or over each pharmacy store/pharmacy computer 104 corresponding to a pharmacy, as exemplified in FIGS. 4 and 6 respectively. Referring to FIG. 4, in such example embodiments, the exemplary linking index would contain only one claims processor ID (.e.g., there would be a distinct linking index associated with each claims processor). Referring to FIG. 6, the exemplary linking index can include, for example, an NPI number for a pharmacy store, if the linking index is established over a single pharmacy store, an NPI number and pharmacy chain identifier, if the linking index is established over a single pharmacy store of a pharmacy chain, or a pharmacy chain identifier, if the linking index is established over a pharmacy. Continuing with the previous example, to agglomerate patient medication history data over a preselected combination of pharmacies/pharmacy computer 104 and claims processors/claims processor computer 106, the aggregation module 130 can apply method 700 to each preselected claims processor/claims processor computer 106 and can apply steps 708-724 for each preselected pharmacy/pharmacy computer 104 (or each pharmacy store). In such an example, aggregation module 130 can identify the linking indexes for each of the preselected pharmacies/pharmacy computer 104 (or for each store thereof) based at least in part upon the pharmacy identifiers in the linking indexes. Furthermore, aggregation module 130 can identify the linking indexes for each of the preselected claims processors/claims processor computer 106 from the claims processor ID in the linking indexes.

In some example embodiments, service provider computer can chronologically arrange the agglomerated patient medication history data (e.g., resulting from method 700) to generate the individual's longitudinal medication history. In some embodiments, generation of the longitudinal medication history can be based at least in part on date of service data included in each patient medication history record, as described above. In some such embodiments, the agglomerated patient medication history can be stored in data files 140 and indexed and/or arranged over a time period from most recent date of service to least recent date of service or from least recent date of service to most recent date of service.

Various block and/or flow diagrams of systems, methods, apparatus, and/or computer program products according to example embodiments of the disclosure are described above. It will be understood that one or more blocks of the block diagrams and steps of the flow diagrams, and combinations of blocks in the block diagrams and combinations of steps in the flow diagrams, respectively, can be implemented by computer-executable program instructions. Likewise, some blocks of the block diagrams and steps of the flow diagrams may not necessarily need to be performed in the order presented, or may not necessarily need to be performed at all, according to some embodiments.

These computer-executable program instructions may be loaded onto a special-purpose computer or other particular machine, one or more processors, or other programmable data processing apparatus to produce a particular machine, such that the instructions that execute on the computer, processor, or other programmable data processing apparatus create means for implementing one or more functions specified in the flow diagram step or steps. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram step or steps. As an example, various embodiments of the disclosure may provide for a computer program product including a computer-usable medium having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram step or steps.

Accordingly, blocks of the block diagrams and steps of the flow diagrams support combinations of means for performing the specified functions, combinations of elements or steps for performing the specified functions, and program instruction means for performing the specified functions. It will also be understood that each block of the block diagrams and step of the flow diagrams, and combinations of blocks in the block diagrams and steps of the flow diagrams, can be implemented by special-purpose, hardware-based computer systems that perform the specified functions, elements or steps, or combinations of special-purpose hardware and computer instructions.

Many modifications and other embodiments of the disclosure set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method comprising:
   receiving, by one or more service provider computers associated with a service provider and on behalf of a patient, consent to generate a longitudinal medication history for the patient across one or more selected pharmacies from among a plurality of pharmacies and one or more selected claims processors from among a plurality of claims processors;
   receiving, by the one or more service provider computers, a plurality of patient identification data for the patient;
   generating, by the one or more service provider computers, a patient identification key comprising at least a portion of the received plurality of patient identification data, wherein the plurality of patient identification data comprises patient date of birth, patient cardholder ID, and patient person code;
   identifying, by the one or more service provider computers, a first claims processor identifier for one of the one or more claims processors;
   parsing, by the one or more service provider computers, a plurality of linking indexes in a database, wherein each linking index comprises a claims processor patient identifying key and at least one second claims processor identifier;
   determining, by the one or more service provider computers, at least one linking index comprising a second claims processor identifier matching the first claims processor identifier and a claims processor patient identifying key matching at least a portion of the patient identification key;
   computing a probabilistic similarity between the claims processor patient identifying key and the patient identifying key;
   identifying, by the one or more service provider computers, a claims processor patient identifier for the patient in the at least one matching linking index;
   accessing, by the one or more service provider computers using a routing table maintained by memory accessible to the service provider computer that identifies where to route different requests and based at least on the claims processor patient identifier, a first patient medication history for the patient; and
   generating, by the one or more service provider computers and based at least in part on the first patient medication history for the patient in response to the probabilistic similarity between the claims processor patient identifying key and the patient identifying key satisfying a predetermined threshold, the longitudinal medication history for the patient.

2. The computer-implemented method of claim 1, further comprising:
   identifying, by the one or more service provider computers, a pharmacy identifier for one of the one or more pharmacies;
   comparing, by the one or more service provider computers, the patient identification key and the pharmacy identifier to a second plurality of linking indexes comprising pharmacy patient identifying keys and pharmacy identifiers to determine if the patient identification key and the pharmacy identifier match the pharmacy identifier and at least a portion of the pharmacy patient identifying key in one of the second plurality of linking indexes;
   selecting, by the one or more service provider computers and based on a positive determination that the patient identification key and the pharmacy identifier match at least a portion of the data in one of the second plurality of linking indexes, a longitudinal identifier for the patient in the matching linking index;
   retrieving, by the one or more service provider computers and based on the pharmacy identifier, a second set of patient medication history data for the patient from the matching linking index;
   wherein the longitudinal medication history for the patient is generated based at least on the first patient medication history and the second set of patient medication history data.

3. The computer-implemented method of claim 2, wherein the one or more claims processor patient identifying keys and one or more pharmacy patient identifying keys comprise key fields associated with patient identification data and wherein the claims processor patient identifying key values and pharmacy patient identifying key values comprise patient identification data for the patient.

4. The computer-implemented method of claim 3, wherein the one or more claims processor patient identifying keys and one or more matching pharmacy patient identifying keys comprise one or more common key fields and one or more matching key values corresponding to the one or more key fields.

5. The computer-implement method of claim 1, further comprising:
   determining, by the one or more service provider computers, if the at least one matching linking index includes at least one other claims processor identifier different from the first claims processor identifier;
   identifying, by the one or more service provider computers and based on a positive determination that the at least one matching linking index includes at least one other claims processor identifier different from the first claims processor identifier, a second claims processor patient identifier for the patient and associated with the at least one other claims processor identifier in the at least one matching linking index; and accessing, by the one or more service provider computers and based at least on the claims processor patient identifier, a second patient medication history data for the patient; and wherein the longitudinal medication history for the patient is generated based at least on the first patient medication history and the second patient medication history data.

6. A computer-implemented method comprising:

generating, by one or more service provider computers associated with a service provider and based upon claims processor identifiers for one or more claims processors and patient identification data for a first plurality of patients, one or more claims processor linking indexes associated with a first patient of the first plurality of patients and comprising separate fields for a claims processor identifier identifying one of a plurality of claims processors, a claims processor patient identifier identifying the first patient, and one or more claims processor patient identifying keys, wherein the one or more claims processor patient identifying keys comprise one or more claims processor patient identifying key fields and corresponding claims processor patient identifying key values, wherein the claims processor patient identifying key fields correspond to patient identification data for the first patient, and wherein the corresponding claims processor patient identifying key values are generated from the patient identification data for the first patient;

generating, by the one or more service provider computers and based upon pharmacy identifiers for one or more pharmacies and patient identification data for a second plurality of patients, one or more pharmacy linking indexes associated with the first patient and comprising separate fields for a pharmacy identifier identifying one of the one or more pharmacies and one or more pharmacy patient identifying keys, wherein the one or more pharmacy patient identifying keys comprise one or more pharmacy patient identifying key fields and corresponding pharmacy patient identifying key values, wherein the pharmacy patient identifying key fields correspond to patient identification data, and wherein the corresponding pharmacy patient identifying key values are generated from the patient identification data for the first patient, computing a probabilistic similarity between the claims processor patient identifying key for the first patient and the pharmacy patient identifying key for the first patient; and generating, by the one or more service provider computers and in response to receiving consent on behalf of the individual and in response to the probabilistic similarity between the claims processor patient identifying key for the first patient and the pharmacy patient identifying key for the first patient satisfying a predetermined threshold, a longitudinal medication history for the first patient, wherein the generating is based at least in part on at least one of the one or more of the claims processor linking indexes and at least one of the one or more pharmacy linking indexes.

7. The computer implemented method of claim 6, wherein for at least one of the one or more claims processor linking indexes, the generating comprises:

identifying, by the one or more service provider computers, patient identification data for the first patient and patient identification data for a second patient from patient identification data associated with the one or more claims processors;

applying, by the one or more service provider computers, probabilistic matching techniques to the patient identification data for the first patient and the patient identification data for the second patient to calculate an overall matching score;

comparing, by the one or more service provider computers, the overall matching score to a matching threshold score;

determining, by the one or more service provider computers that the overall matching score satisfies the matching threshold score;

determining, by the one or more service provider computers and based at least in part on the overall matching score satisfying the matching threshold score, that the patient identification data for the first patient and the patient identification data for the second patient each are for the first patient, generating, by the one or more service provider computers, a second claims processor patient identifying key for the second patient, based at least in part on the patient identification data for the second patient and adding the second claims processor patient identifying key for the second patient to the at least one of the claims processor linking indexes for the first patient.

8. The method of claim 6, wherein the claims processor patient identifying key fields correspond to demographic data and/or billing data and wherein the corresponding claims processor patient identifying key values are generated from the patient identification data for the first patient and from the one or more claims processors.

9. The method of claim 8, wherein the pharmacy patient identifying key fields correspond to demographic data and/or billing data and wherein the corresponding pharmacy patient identifying key values are generated from the patient identification data for the first patient and from the one or more pharmacies.

10. The computer implemented method of claim 9, wherein at least one of generating one or more claims processor linking indexes and generating one or more pharmacy linking indexes is performed prior to the receiving the consent on behalf of the user.

11. A system comprising:

at least one memory operable to store computer-executable instructions and at least one processor configured to access the at least on memory and execute the computer-executable instructions to:

receive, on behalf of a patient, consent to generate a longitudinal medication history for the patient across one or more pharmacies and one or more claims processors;

receive a plurality of patient identification data for the patient;

generate a patient identification key comprising at least a portion of the received plurality of patient identification data wherein the plurality of patient identification data comprises patient date of birth, patient cardholder ID, and patient person code;

identify a first claims processor identifier for one of the one or more claims processors;

parse a plurality of linking indexes in a database, wherein each linking index comprises a claims processor patient identifying key and at least one second claims processor identifier;

determine at least one linking index comprising a second claims processor identifier matching the first claims processor identifier and a claims processor patient identifying key matching at least a portion of the patient identification key;

compute a probabilistic similarity between the claims processor patient identifying key and the patient identifying key;

identify a claims processor patient identifier for the patient in the at least one matching linking index;

access, based at least on the claims processor patient identifier, a first patient medication history for the patient; and generate, based at least in part on the first patient medication history for the patient and in response to the probabilistic similarity between the claims processor patient identifying key and the patient identifying key satisfying a predetermined threshold, the longitudinal medication history for the patient.

12. The system of claim 11, wherein the at least one processor is further configured to access the at least one memory and execute the computer-executable instructions to:

identify a pharmacy identifier for one of the one or more pharmacies;

compare the patient identification key and the pharmacy identifier to a second plurality of linking indexes comprising pharmacy patient identifying keys and pharmacy identifiers to determine if the patient identification key and the pharmacy identifier match the pharmacy identifier and at least a portion of the pharmacy patient identifying key in one of the second plurality of linking indexes;

select, based on a positive determination that the patient identification key and the pharmacy identifier match at least a portion of the data in one of the second plurality of linking indexes, a longitudinal identifier for the patient in the matching linking index;

retrieve, based on the pharmacy identifier, a second set of patient medication history data for the patient from the matching linking index;

wherein the longitudinal medication history for the patient is generated based at least on the first patient medication history and the second set of patient medication history data.

13. The system of claim 12, wherein the one or more claims processor patient identifying keys and one or more pharmacy patient identifying keys comprise key fields associated with patient identification data and wherein the claims processor patient identifying key values and pharmacy patient identifying key values comprise patient identification data for the patient.

14. The system of claim 13, wherein the one or more claims processor patient identifying keys and one or more matching pharmacy patient identifying keys comprise one or more common key fields and one or more matching key values corresponding to the one or more key fields.

15. The system of claim 12, wherein the at least one processor is further configured to access the at least one memory and execute the computer-executable instructions to:

determine if the at least one matching linking index includes at least one other claims processor identifier different from the first claims processor identifier;

identify, based on a positive determination that the at least one matching linking index includes at least one other claims processor identifier different from the first claims processor identifier, a second claims processor patient identifier for the patient and associated with the at least one other claims processor identifier in the at least one matching linking index; and access, based at least on the claims processor patient identifier, a second patient medication history data for the patient; and wherein the longitudinal medication history for the patient is generated based at least on the first patient medication history and the second patient medication history data.

16. A system comprising:

at least one memory operable to store computer-executable instructions and at least one processor configured to access the at least one memory and execute the computer-executable instructions to:

generate, based upon identification data associated with one or more claims processors and a first plurality of patients, one or more claims processor linking indexes associated with a first patient of the first plurality of patients and comprising separate fields for a claims processor identifier identifying one of a plurality of claims processors, a claims processor patient identifier identifying the first patient, and one or more claims processor patient identifying keys, wherein the one or more claims processor patient identifying keys comprise one or more claims processor patient identifying key fields and corresponding claims processor patient identifying key values, wherein the claims processor patient identifying key fields correspond to patient identification data for a patient, and wherein the corresponding claims processor patient identifying key values are generated from the patient identification data for the first patient;

generate, based upon pharmacy identifiers for one or more pharmacies and patient identification data for a second plurality of patients, one or more pharmacy linking indexes associated with the first patient and comprising separate fields for a pharmacy identifier identifying a selected one of the one or more pharmacies and selected one or more pharmacy patient identifying keys, wherein the selected one or more pharmacy patient identifying keys comprise one or more pharmacy patient identifying key fields and corresponding pharmacy patient identifying key values, wherein the pharmacy patient identifying key fields correspond to patient identification data, and wherein the corresponding pharmacy patient identifying key values are generated from the patient identification data for the first patient and from the at least one of the one or more pharmacies;

compute a probabilistic similarity between the claims processor patient identifying key for the first patient and the pharmacy patient identifying key for the first patient; and generate, in response to receiving consent on behalf of the individual and in response to the probabilistic similarity between the claims processor patient identifying key for the first patient and the pharmacy patient identifying key for the first patient satisfying a predetermined threshold, a longitudinal medication history for the first patient, wherein the generating is based at least in part on at least one of the one or more of the claims processor linking indexes and at least one of the one or more pharmacy linking indexes.

17. The system of claim 16, wherein for at least one of the one or more claims processor linking indexes, the at least one processor is further configured to access the at least one memory and execute the computer-executable instructions to:

identify patient identification data for first patient and patient identification data for a second patient from patient identification data received from the one or more claims processors;

apply probabilistic matching techniques to the patient identification data for the first patient and the patient identification data for the second patient to calculate an overall matching score;

compare the overall matching score to a matching threshold score;

determine that the overall matching score satisfies the matching threshold score;

determine, based at least in part on the overall matching score satisfying the matching threshold score, that the patient identification data for the first patient and the patient identification data for the second patient each identify the first patient, generate a second claims processor patient identifying key for the second patient, based at least in part on the patient identification data for the second patient and add the second claims processor patient identifying key for the second patient to the at least one of the claims processor linking indexes for the first patient.

18. The system of claim 16, wherein the claims processor patient identifying keys comprise claims processor patient identifying key fields corresponding to demographic data and/or billing data and wherein the corresponding claims processor patient identifying key values are generated from the patient identification data for the first patient and from the one or more claims processors.

19. The system of claim 18, wherein the pharmacy patient identifying keys comprise pharmacy patient identifying key fields corresponding to demographic data and/or billing data and wherein the corresponding pharmacy patient identifying key values are generated from the patient identification data for the first patient and from the one or more pharmacies.

20. The system of claim 19, wherein at least one of generating one or more claims processor linking indexes and generating one or more pharmacy linking indexes is performed prior to the receiving the consent on behalf of the user.

* * * * *